(12) United States Patent
Carron et al.

(10) Patent No.: US 9,494,581 B2
(45) Date of Patent: Nov. 15, 2016

(54) SYSTEM AND METHOD FOR RAMAN SPECTROSCOPY ASSAY USING PARAMAGNETIC PARTICLES

(75) Inventors: Keith T. Carron, Centennial, WY (US); Bryan H. Ray, Laramie, WY (US)

(73) Assignee: University of Wyoming, Laramie, WY (US)

( * ) Notice: Subject to any disclaimer, the term of this patent is extended or adjusted under 35 U.S.C. 154(b) by 1059 days.

(21) Appl. No.: 11/211,325

(22) Filed: Aug. 24, 2005

(65) Prior Publication Data

US 2006/0240572 A1 Oct. 26, 2006

Related U.S. Application Data

(60) Provisional application No. 60/604,267, filed on Aug. 24, 2004.

(51) Int. Cl.
*G01N 33/553* (2006.01)
*G01N 33/543* (2006.01)
*G01N 21/65* (2006.01)

(52) U.S. Cl.
CPC ...... *G01N 33/54326* (2013.01); *G01N 21/658* (2013.01); *G01N 33/54353* (2013.01); *G01N 2021/651* (2013.01)

(58) Field of Classification Search
CPC ... G01J 3/44; G01N 21/65; G01N 33/54346; G01N 15/1434; G01N 15/147
USPC ............ 436/518, 526, 164, 171, 805; 435/4, 435/969
See application file for complete search history.

(56) References Cited

U.S. PATENT DOCUMENTS

| 3,933,997 A | 1/1976 | Hersh |
| 3,985,649 A | 10/1976 | Eddelman |
| 4,070,246 A | 1/1978 | Kennedy |
| 5,108,933 A | 4/1992 | Liberti |
| 5,266,498 A | 11/1993 | Tarcha et al. |
| 5,375,606 A | 12/1994 | Slezak |

(Continued)

FOREIGN PATENT DOCUMENTS

| WO | WO8903533 | 4/1989 |
| WO | WO2007005540 | 1/2007 |

OTHER PUBLICATIONS

Pedro Tartaj et.al., Topical Review, "The Preparation of Magnetic Nanoparticles for Applications in Biomedicine", Journal of Physics D: Applied Physics; 36 (2003) R182-R197.

(Continued)

*Primary Examiner* — Mark Shibuya
*Assistant Examiner* — Pensee Do
(74) *Attorney, Agent, or Firm* — Dinsmore & Shohl, LLP

(57) ABSTRACT

A Raman spectroscopy technique allows an analyte, a paramagnetic particle, and a spectral enhancement particle to combine in solution and for the combination product to be localized by a magnetic field for analysis. The spectral enhancement particle may be comprised of an active SERS metal particle with or without a material coating. The spectral enhancement particle may function as a reporter for the presence of the analyte or merely increase the magnitude of the Raman spectrum of the analyte. The technique is applicable to both immunoassays and chemical assays. Multiple spectral enhancement particle reporters may be measured in a single assay that can detect multiple analytes using the SERS effect.

18 Claims, 26 Drawing Sheets

(56) References Cited

U.S. PATENT DOCUMENTS

| | | | |
|---|---|---|---|
| 5,376,556 A | 12/1994 | Tarcha et al. | |
| 5,378,508 A | 1/1995 | Castro et al. | |
| 5,445,971 A | 8/1995 | Rohr | |
| 5,536,644 A | 7/1996 | Ullman | |
| 5,567,628 A | 10/1996 | Tarcha et al. | |
| 5,609,907 A | 3/1997 | Natan | |
| 5,633,168 A * | 5/1997 | Glasscock et al. | 436/52 |
| 5,693,152 A * | 12/1997 | Carron | G01N 21/658 |
| | | | 148/271 |
| 5,814,516 A | 9/1998 | Vo-Dinh | |
| 6,013,532 A | 1/2000 | Liberti | |
| 6,025,202 A | 2/2000 | Natan | |
| 6,149,868 A | 11/2000 | Natan et al. | |
| 6,174,677 B1 | 1/2001 | Vo-Dinh | |
| 6,180,415 B1 | 1/2001 | Schultz | |
| 6,214,560 B1 | 4/2001 | Yguerabide et al. | |
| 6,219,137 B1 | 4/2001 | Vo-Dinh | |
| 6,242,264 B1 | 6/2001 | Natan et al. | |
| 6,254,830 B1 | 7/2001 | Pivarnik | |
| 6,258,607 B1 | 7/2001 | Saito | |
| 6,325,973 B1 * | 12/2001 | Leland et al. | 422/52 |
| 6,337,215 B1 | 1/2002 | Wilson | |
| 6,342,396 B1 | 1/2002 | Perrin | |
| 6,361,944 B1 | 3/2002 | Mirkin et al. | |
| 6,365,362 B1 * | 4/2002 | Terstappen et al. | 435/7.23 |
| 6,417,340 B1 | 7/2002 | Mirkin et al. | |
| 6,495,324 B1 | 12/2002 | Mirkiin et al. | |
| 6,506,564 B1 | 1/2003 | Mirkin et al. | |
| 6,514,767 B1 | 2/2003 | Natan | |
| 6,537,829 B1 | 3/2003 | Zarling | |
| 6,558,956 B1 | 5/2003 | Carron et al. | |
| 6,579,721 B1 | 6/2003 | Natan et al. | |
| 6,579,726 B1 | 6/2003 | Natan et al. | |
| 6,582,921 B2 | 6/2003 | Mirkin et al. | |
| 6,586,193 B2 | 7/2003 | Yguerabide | |
| 6,610,491 B2 | 8/2003 | Mirkin et al. | |
| 6,624,886 B2 | 9/2003 | Natan et al. | |
| 6,630,355 B1 | 10/2003 | Pivarnik | |
| 6,645,721 B2 | 11/2003 | Mirkin et al. | |
| 6,645,777 B1 | 11/2003 | Letcher | |
| 6,673,548 B2 | 1/2004 | Mirkin et al. | |
| 6,677,122 B2 | 1/2004 | Mirkin et al. | |
| 6,682,895 B2 | 1/2004 | Mirkin et al. | |
| 6,709,825 B2 | 3/2004 | Mirkin et al. | |
| 6,720,147 B2 | 4/2004 | Mirkin et al. | |
| 6,720,411 B2 | 4/2004 | Mirkin et al. | |
| 6,730,269 B2 | 5/2004 | Mirkin et al. | |
| 6,740,491 B2 | 5/2004 | Mirkin et al. | |
| 6,750,016 B2 | 6/2004 | Mirkin et al. | |
| 6,750,065 B1 | 6/2004 | White | |
| 6,759,199 B2 | 7/2004 | Mirkin et al. | |
| 6,767,702 B2 | 7/2004 | Mirkin et al. | |
| 6,770,488 B1 | 8/2004 | Carron et al. | |
| 6,773,884 B2 | 8/2004 | Mirkin et al. | |
| 6,777,186 B2 | 8/2004 | Mirkin et al. | |
| 6,812,334 B1 | 11/2004 | Mirkin et al. | |
| 6,818,753 B2 | 11/2004 | Mirkin et al. | |
| 6,828,432 B2 | 12/2004 | Mirkin et al. | |
| 6,844,199 B1 | 1/2005 | Nelson | |
| 6,858,440 B1 | 2/2005 | Letcher | |
| 6,861,221 B2 | 3/2005 | Mirkin et al. | |
| 6,861,263 B2 | 3/2005 | Natan | |
| 6,878,814 B2 | 4/2005 | Mirkin et al. | |
| 6,902,895 B2 | 6/2005 | Mirkin et al. | |
| 6,903,207 B2 | 6/2005 | Mirkin et al. | |
| 6,962,786 B2 | 11/2005 | Mirkin et al. | |
| 6,969,761 B2 | 11/2005 | Mirkin et al. | |
| 6,984,491 B2 | 1/2006 | Mirkin et al. | |
| 6,986,989 B2 | 1/2006 | Mirkin et al. | |
| 7,098,320 B1 | 8/2006 | Mirkin et al. | |
| 7,135,055 B2 | 11/2006 | Mirkin et al. | |
| 7,147,687 B2 | 12/2006 | Mirkin et al. | |
| 7,169,556 B2 | 1/2007 | Mirkin et al. | |
| 7,192,778 B2 | 3/2007 | Natan | |
| 7,208,587 B2 | 4/2007 | Mirkin et al. | |
| 7,225,082 B1 | 5/2007 | Natan et al. | |
| 7,238,472 B2 | 7/2007 | Mirkin et al. | |
| 7,250,499 B2 | 7/2007 | Mirkin et al. | |
| 7,255,995 B2 | 8/2007 | Yguerabide et al. | |
| 2001/0002315 A1 | 5/2001 | Schultz | |
| 2001/0029752 A1 | 10/2001 | Natan et al. | |
| 2002/0034827 A1 | 3/2002 | Singh et al. | |
| 2002/0086335 A1 | 7/2002 | Massey | |
| 2002/0104762 A1 | 8/2002 | Stonas et al. | |
| 2002/0106708 A1 * | 8/2002 | Thomas et al. | 435/7.93 |
| 2002/0142480 A1 | 10/2002 | Natan | |
| 2002/0146745 A1 | 10/2002 | Natan et al. | |
| 2002/0164825 A1 | 11/2002 | Chen | |
| 2003/0017620 A1 | 1/2003 | Carron | |
| 2003/0029274 A1 | 2/2003 | Natan et al. | |
| 2003/0059955 A1 | 3/2003 | Bamdad | |
| 2003/0082589 A1 * | 5/2003 | Chan et al. | 435/6 |
| 2003/0096302 A1 | 5/2003 | Yguerabide | |
| 2003/0112432 A1 | 6/2003 | Yguerabide | |
| 2003/0139886 A1 | 7/2003 | Bodzin | |
| 2003/0157732 A1 | 8/2003 | Baker et al. | |
| 2003/0166297 A1 | 9/2003 | Natan | |
| 2003/0209427 A1 | 11/2003 | Natan et al. | |
| 2004/0178076 A1 | 9/2004 | Stonas et al. | |
| 2004/0209376 A1 | 10/2004 | Natan et al. | |
| 2005/0019556 A1 | 1/2005 | Freeman et al. | |
| 2005/0032226 A1 | 2/2005 | Natan | |
| 2005/0048672 A1 * | 3/2005 | Luxton et al. | 436/526 |
| 2005/0064435 A1 * | 3/2005 | Su et al. | 435/6 |
| 2005/0130163 A1 | 6/2005 | Smith | |
| 2005/0248758 A1 | 11/2005 | Carron | |
| 2006/0054506 A1 | 3/2006 | Natan | |
| 2006/0135861 A1 * | 6/2006 | Lucassen et al. | 600/315 |
| 2006/0205093 A1 * | 9/2006 | Prins | 436/526 |
| 2006/0216697 A1 | 9/2006 | Mondello et al. | |
| 2006/0216835 A1 | 9/2006 | Mondello | |
| 2006/0262304 A1 | 11/2006 | Carron | |

OTHER PUBLICATIONS

Carron et al., Octadecylthiol-Modified Surface-Enhanced Raman Spectroscopy Substrates: A New Method for the Detection of Aromatic Compounds, Environ. Sci Technol. 1992, 26, 1950-1954.

Mullen and Carron, Adsorption of Chlorinated Ethylenes at 1-Octadecanethiol-Modified Silver Surfaces, Anal. Chem., 1994, 66, 478-483.

Crane, et al., SERS Surfaces Modified with a 4-(2-Pyridylazo)resorcinol Disulfide Derivative: Detection of Copper, Lead, and Cadmium, Anal. Chem., 1995, 67, 360-364.

Kennedy et al., Development of a Cascade Flow Cell for Dynamic Aqueous Phase Detection Using Modified SERS Substrates, Anal. Chem. 1997, 69, 4708-4715.

* cited by examiner

SYSTEM AND METHOD FOR RAMAN SPECTROSCOPY ASSAY USING PARAMAGNETIC PARTICLES

CROSS-REFERENCE TO RELATED APPLICATIONS

This application claims priority pursuant to 35 U.S.C. §119(e) to U.S. provisional application No. 60/604,267 filed 24 Aug. 2004, which is hereby incorporated herein by reference in its entirety.

BACKGROUND OF THE INVENTION

1. Field of the Invention

This invention relates to chemical and biochemical analysis using surface-enhanced Raman spectroscopy and, more particularly, it relates to the use of paramagnetic particles to spatially localize an analyte in the presence of a spectral enhancement particle for chemical and biochemical analyses.

2. Description of the Related Art

Raman spectroscopy finds its origins in Planck and Einstein's formulation that light is not only wavelike in nature, but has the dual character of waves and particles. Once scientists began thinking about the concept of light as particles, the possibility of inelastic scattering of these particles became a method of proof of this new theory. In 1923 Compton showed this with inelastic scattering of x-rays from a graphite target. That same year Smekal theoretically predicted that photons should inelastically scatter from molecular transitions. Five years later, in 1928, C. V. Raman and K. S. Krishnan published an article in the journal Nature with experiments that proved Smekal's prediction of inelastic scattering of light. For his discovery, Raman was award the Nobel Prize and the inelastic scattering of visible light from molecular transitions has been named after him.

When light is scattered from a molecule most photons are elastically scattered. The scattered photons have the same energy (frequency) and, therefore, wavelength, as the incident photons. However, a small fraction of light (approximately 1 in 107 photons) is scattered at optical frequencies different from, and usually lower than, the frequency of the incident photons. The process leading to this inelastic scatter is the termed the Raman effect. Raman scattering can occur with a change in vibrational, rotational or electronic energy of a molecule. The difference in energy between the incident photon and the Raman scattered photon is equal to the energy of a vibration of the scattering molecule. A plot of intensity of scattered light versus energy difference is a Raman spectrum.

The Raman effect arises when a photon is incident on a molecule and interacts with the electric dipole of the molecule. It is a form of electronic (more accurately, vibronic) spectroscopy, although the spectrum contains vibrational frequencies. In classical terms, the interaction can be viewed as a perturbation of the molecule's electric field. In quantum mechanics the scattering is described as an excitation to a virtual state lower in energy than a real electronic transition with nearly coincident de-excitation and a change in vibrational energy. The scattering event occurs in $10^{-14}$ seconds or less.

One of the characteristics of inelastic scattering is that the intensity of the scattering scales to the fourth power of the energy. This means that Compton's experiments with X-rays with a wavelength of 0.7 nm and the observation of Raman scattering with visible light at 500 nm will differ by 11 orders of magnitude. Raman was able to observe the weak Raman effect by using the most intense light source available at the time, the sun. He focused a large telescope on the sun and placed a green filter in the intense beams of sunlight. When he used a yellow filter to observe this beam of green light passing through a solution of chloroform, he could see a weak yellow light. The origin of the yellow light was the Raman effect. A small amount of the green light from the sun had inelastically scattered from the chloroform molecules and shifted its energy so that the photons fell within the yellow part of the spectrum.

The Raman effect is observed as a shift in energy of a photon and the shift can be related to a vibrational state of the sample. To observe the shift all of the photons need to be within a very narrow band of energies, otherwise, it is difficult to distinguish the shifted photons from the source photons. Raman spectroscopy is conventionally performed with a green, red or near-infrared laser. The laser produces quasi-monochromatic light that forms a very narrow band of wavelengths. The laser also produces this light in a small concentrated beam that is very intense. The wavelength of the laser is below the first electronic transitions of most molecules, as assumed by scattering theory. However, if the wavelength of the exciting laser is within the electronic spectrum of a molecule, the intensity of some Raman-active vibrations increases by a factor of $10^2$-$10^4$. This resonance enhancement or resonance Raman effect can be quite useful.

The Raman scattering from a compound (or ion) adsorbed on or even within a few Angstroms of a structured noble metal surface can be $10^3$-$10^{15}$ times greater than in solution. This surface-enhanced Raman scattering (SERS) is strongest on silver and gold, but is observable on copper as well. At practical excitation wavelengths, significant enhancement on other metals has not been observed.

Surface-enhanced Raman scattering arises from two mechanisms. The first is an enhanced electromagnetic field produced at the surface of the metal. When the wavelength of the incident light is close to the plasma wavelength of the metal, conduction electrons in the metal surface are excited into an extended surface electronic excited state called a surface plasmon resonance. Molecules adsorbed on or in close proximity to the surface experience an exceptionally large electromagnetic field. Vibrational modes normal to the surface are most strongly enhanced. The second mode of enhancement is by the formation of a charge-transfer complex between the surface and analyte molecule. The electronic transitions of many charge transfer complexes are in the visible spectrum leading to resonance enhancement.

The intensity of the surface plasmon resonance is dependent on many factors including the wavelength of the incident light and the morphology of the metal surface. The wavelength should match the plasma wavelength of the metal. This is about 382 nm for a 5 μm silver particle, but can be much higher for larger ellipsoidal silver particles. The plasma wavelength is to the red of 550 nm (i.e., wavelengths greater than 550 nm) for copper and gold, the other two metals which show SERS at wavelengths in the 350-1000 nm region. The best morphology for surface plasmon resonance excitation is a small (<100 nm) particle or an atomically rough surface.

Molecules with lone pair electrons or pi clouds show the strongest SERS. The effect was first discovered with pyridine. Other aromatic nitrogen or oxygen containing compounds, such as aromatic amines or phenols, are strongly SERS active. The effect can also been seen with other electron-rich functionalities such as carboxylic acids.

SERS is used to study monolayers of materials adsorbed on metals, including electrodes. Many formats other than electrodes can be used. The most popular include colloids, metal films on dielectric substrates, and arrays of metal particles bound to metal or dielectric colloids through short linkages. Although SERS allows easy observation of Raman spectra from solution concentrations in the micromolar ($1\times10^6$) range, slow adsorption kinetics and competitive adsorption limit its application in analytical chemistry.

In 1991 Carron, et al., demonstrated that SERS surfaces could be used to detect trace amounts of materials. (See Ultrasensitive Detection of Metal Ions with Surface Enhanced Raman Spectroscopy. K. Carron, K. Mullen, H. Angersbach, and M. Lanouette, *Appl. Spectrosc.*, 45:420 (1991).) This introduces the concept of a coating on a SERS particle that has an affinity for an analyte. Carron defined three types of coatings: passive, active, and reactive. A passive coating creates an affinity for an analyte and the analyte is detected from the analyte's Raman spectrum. Passive coatings attract the analyte in a reversible fashion. An active coating has an affinity for an analyte and the analyte is detected through a change in the spectrum of the coating. Active coatings also bind the analyte reversibly. A reactive coating reacts with the analyte and produces a new molecular coating that has incorporated the analyte into its chemical structure. In this case, the analyte is detected by a change in the Raman spectrum of the coating. Reactive coatings bind the analyte irreversibly.

In 1993 Tarcha, et al., U.S. Pat. No. 5,266,498, the applicants describe a similar approach using an antibody on a SERS surface to act as an affinity. This reference discloses applying an antibody to a SERS surface. The antibody on the SERS surface, in turn, binds to an analyte. After the analyte is bound to the antibody on the surface of a SERS particle, a second antibody having a resonance Raman active dye conjugated to it is added. The second antibody also has an affinity for the analyte and similarly binds to the analyte. Traditionally this is known as a sandwich assay. When the dye bound to the second antibody is near the SERS active surface, a Raman spectral signal of the dye is observed.

The information included in this Background section of the specification, including any references cited herein and any description or discussion thereof, is included for technical reference purposes only and is not to be regarded subject matter by which the scope of the invention is to be bound.

SUMMARY OF THE INVENTION

The present invention provides a novel SERS technique that allows an analyte, a paramagnetic particle, and a spectral enhancement particle to combine in solution and for the combination product to be localized by a magnetic field for analysis. In one form of the invention, the spectral enhancement particle may function as a reporter for the presence of the analyte. The spectral enhancement particle may be comprised of an active SERS metal coated with a material that provides a unique spectrum signature and a material that creates an affinity for the analyte. Raman spectroscopy in general, and specifically SERS, records a different spectrum for different molecular coatings. In another form of the invention, multiple spectral enhancement particle reporters may be measured in a single assay that can detect multiple analytes using the SERS effect. Placement of different coatings on different reporters provides a method to detect multiple analytes in a single measurement. The combination or multiplexing of signatures from different reporters can be deconvoluted to indicate the presence of multiple analytes and to quantitate amounts of analyte. The assay of the present invention can also function in complex matrices and provide an enhanced measurement by magnetic localization without sample preparation. The paramagnetic particles may be used as "engines" powered by a magnetic field to concentrate the analyte into a format readily measured by Raman spectroscopy instrumentation. The small size of these particles allows them to be move through the solution for rapid sampling and to have additional motion for convection through a moving magnetic field. In another form, the invention provides an assay that can continuously sample air or liquids to monitor for analytes.

One form of the invention is a method for performing an assay to determine the presence of an analyte. A plurality of spectral enhancement particles, a plurality of paramagnetic particles, and the analyte are bound together in a solution, when the analyte is present in the solution. A magnetic field is applied to the solution. The plurality of paramagnetic particles are concentrated in a discrete location using the influence of the magnetic field. Further, the discrete location may be interrogated the with a laser light beam. A Raman spectrum is then acquired from Raman scattered light from the discrete location.

In one embodiment of the invention, the assay is an immunoassay wherein the analyte an antigen. In this embodiment, the spectral enhancement particles are connected with a first antibody specific to the antigen and a spectral flag compound. The paramagnetic particles are connected with a second antibody specific to the antigen. The paramagnetic particles are bound to the spectral enhancement particles via the antigen when the spectral enhancement particles with the first antibody and the paramagnetic particles with the second antibody are in the presence of the antigen.

In another embodiment of the invention, the assay is a chemical assay. The solution has a plurality of first tethers, each having a first binding end with an affinity for the spectral enhancement particles and a second binding end with an affinity for the paramagnetic particles. The solution also has a plurality of second tethers, each having a first binding end with an affinity for the spectral enhancement particles and a second binding end with an affinity for the analyte. The paramagnetic particles bind to the spectral enhancement particles via the first tethers. The spectral enhancement particles further bind to the analyte via the second tethers when the analyte is in the solution.

In another form, the invention comprises a method for coupling a paramagnetic particle and a spectral enhancement particle. A plurality of spectral enhancement particles are introduced into a solution. A plurality of paramagnetic particles are also introduced into the solution. A tether is further introduced into the solution. The tether has a first binding end with an affinity for the spectral enhancement particles and a second binding end with an affinity for the paramagnetic particles. The paramagnetic particles are attached to the spectral enhancement particles via the first tether.

A further form of the invention is a Raman spectroscopy assay system. The system comprises a sample chamber, a magnet, a laser, and a Raman analyzer. The magnet is positioned adjacent the sample chamber. A plurality of spectral enhancement particles adapted to bind with an analyte are positioned within the sample chamber. A plurality of paramagnetic particles are also positioned within the sample chamber. The paramagnetic particles are adapted to bind with either the spectral enhancement particles or the analyte and are attracted by a magnetic field generated by the magnet. The laser is aligned with the magnet such that a light beam generated by the laser is directed into the sample chamber to a position where the paramagnetic particles concentrate under the influence of the magnetic field generated by the magnet. The Raman analyzer is positioned to acquire Raman scattered light reflected from the analyte when bound with the plurality of spectral enhancement particles.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 25 is schematic diagram depicting an exemplary chemical tether for joining a neurotransmitter analyte to a spectral enhancement particle.

DETAILED DESCRIPTION OF THE INVENTION

The present invention is

Figure 1:
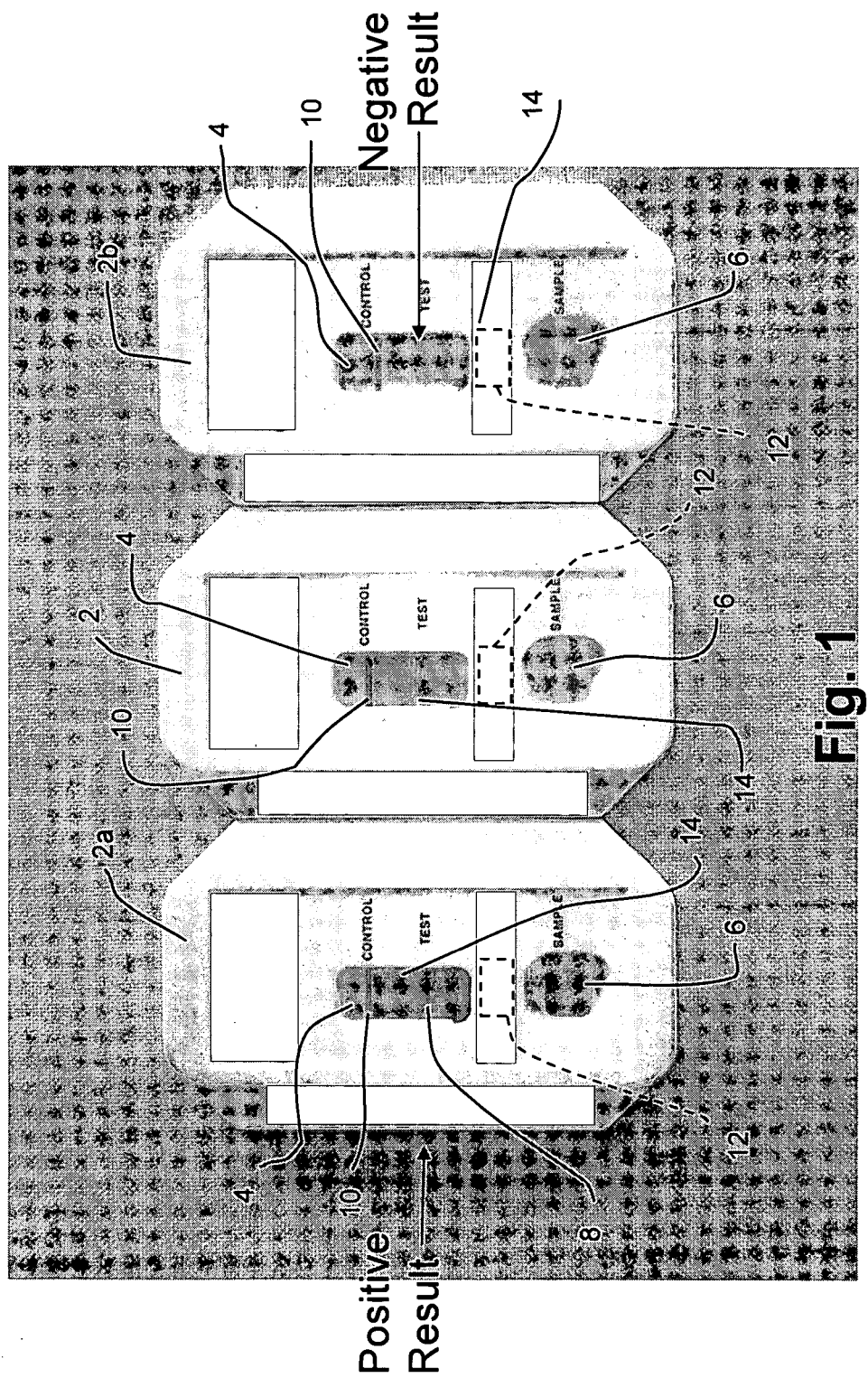
FIG. 1 is a schematic diagram of exemplary prior art lateral flow immunoassay cards.

Prior art FIG. 1 illustrates a current state of the art lateral flow immunoassay. Immunoassay is used primarily to test for the presence of specific antigens within a sample. For example, one common form of lateral flow immunoassay is a home pregnancy test wherein a sample of urine is analyzed on a lateral flow immunoassay card to determine the presence of specific antigens in the urine sample that are indicative of pregnancy. Typically, an immunoassay card 2 houses a fibrous pad 4 that generally extends the length of the immunoassay card 2. An opening at one end of the immunoassay card 2 functions as a sample reservoir 6 for introduction of a sample onto the fibrous pad 4. The sample placed in the sample reservoir 6 is generally a liquid. However, should the desired sample be in the form of a solid, it is initially mixed with a liquid solvent in order for the sample to dissolve into solution.

The liquid sample travels through the fibrous pad 4 from the sample reservoir 6 by capillary action. The sample will first encounter a reagent pad 12 upon which is deposited a compound that is chosen to both bind with potential antigens subject to testing and act as a visual marker to indicate the presence of such antigens. Generally the reagent is composed of a first antibody with an affinity for a desired antigen and a marker bound to the antibody. Common and exemplary markers in reagents used in lateral flow immunoassay are latex or gold nanoparticles bound to antibodies. As a sample flows through the fibrous pad 4, the antigens, now bound to reagent particles by the antibody, continue to flow through the fibrous pad 4 along with the sample.

Figure 2:
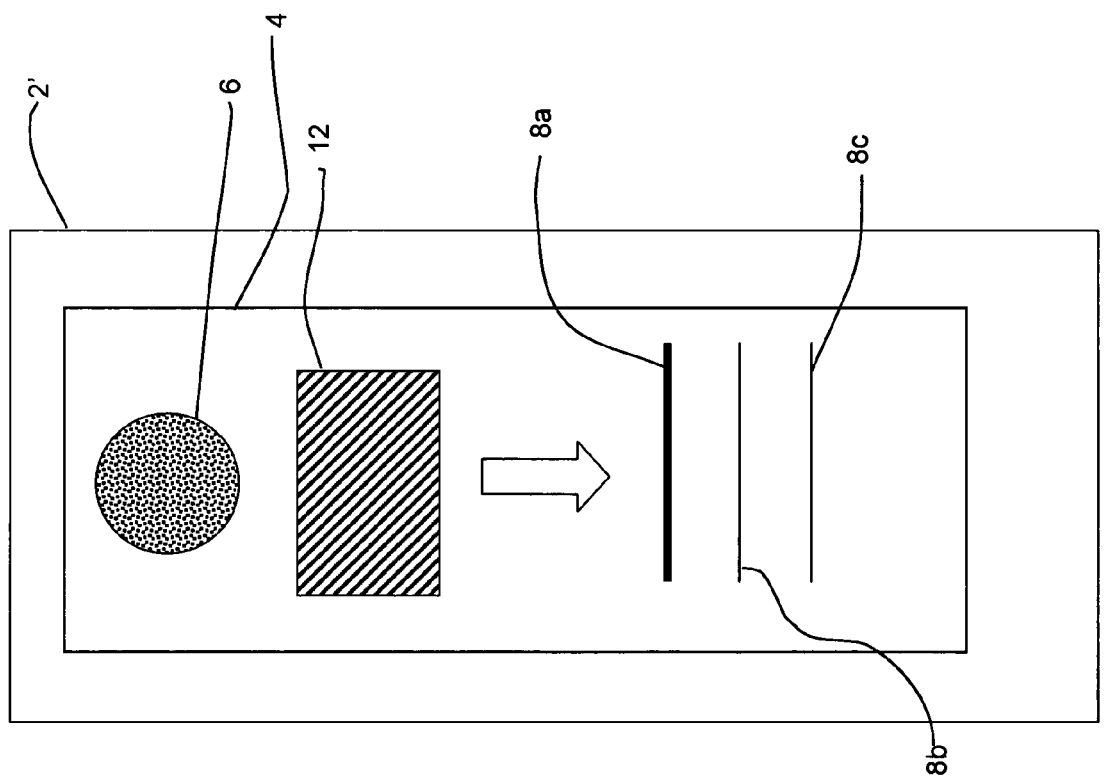
FIG. 2 is a schematic diagram of an exemplary prior art multiplexed lateral flow immunoassay card.

As shown in FIGS. 1 and 2, the sample flow will next encounter a test strip 8. The test strip 8 is an area populated with a receptor for the particular antigen that is the subject of the assay. Generally, the test strip 8 is a strip of nitrocellulose, polyvinylidene fluoride (PVDF), or similar material bound with a second particular antibody type and affixed on the fibrous pad 4. If the sample flowing through the fibrous pad 4 contains an antigen receptive to the second antibody in the test strip 8, then the antibody will bind with the antigen and prevent it from flowing further through the fibrous pad 4. The antigen is thus "sandwiched" between the first antibody and the second antibody. If a desired antigen is present in the sample, the antigen and the associated reagents previously bound to the antigens will collect along the test strip 8. Recalling that one property of a desired reagent is its ability to act as a visual marker, as the antigens bind with the second antibodies on the test strip 8, a large quantity of the reagent will similarly be amassed along the test strip 8 and create a visually perceptive marker to indicate the presence of the antigen in question. As shown in FIG. 1, the immunoassay card 2 is provided with a window 14 through which a portion of the fibrous pad 4 containing the test strip 8 is visible. This allows a user to be visually apprised of the results of the assay.

In addition to the test strip 8, a control strip 10 is also provided on the fibrous pad 4. The control strip 10 is positioned beyond the test strip 8. The control strip 10 is a strip of nitrocellulose, polyvinylidene fluoride (PVDF), or similar material bound with a third particular antibody type and affixed on the fibrous pad 4. There is generally significantly more of the first antibody (bound to the reagent) than can be bound to the second antibodies on the test strip 8 and, therefore, the first antibody bound to the reagent will flow past the test strip 8 along the fibrous pad 4 until it reaches the control strip 10. Similar to the test strip 8, the control strip 10 is formed of an area of nitrocellulose, polyvinylidene fluoride (PVDF), or similar material populated with a third antibody antithetical to the first antibody. The third antibody on the control strip 10 thus binds with the first antibody and, since the first has previously bonded with the reagent, the reagent will create a visible marker along the control strip 10.

The control strip 10 is provided to indicate that the sample fluid has moved completely through the fibrous pad 4 and therefore has already passed the position of the test strip 8. Thus, a user can be assured that a negative assay reading is correct by knowing that the sample has already flowed through the test strip 8 without creating a visual marker. FIG. 1 shows both a positive result immunoassay card 2a indicating a visual marker along both the test strip 8 and the control strip 10, and a negative result immunoassay card 2b wherein only the control strip 10 is populated by the visible marker.

There are several drawbacks to the use of typical lateral flow immunoassay cards. First, because the immunoassay card 2 operates on the principle of visual detection, trace quantities of a particular antigen may be difficult to perceive. This is because an inadequate amount of reagent will ultimately bind along the test strip 8, so little as to be visually imperceptible, and thus fail to indicate the presence of the antigen. In some instances, this could result in a false negative reading. In addition, because the immunoassay card 2 is not highly sensitive, it may be an inadequate tool for performing assays on samples with extremely low levels of a particular antigen.

The second drawback to lateral flow immunoassay cards results from poor registration of the test strip 8 and control strip 10 on the fibrous pad 4. In manufacturing practice, the test strip 8 and control strip 10 are placed on the fibrous pad 4 using conventional printing techniques. In the event that the printing registration is off or the fibrous pad 4 is cut to an improper size, or improperly oriented within the immunoassay card 2, it may be difficult to determine whether a result is positive, negative, or whether the immunoassay card 2 functioned properly at all because of the misplacement of the test strip 8 or the control strip 10.

A third problem with conventional immunoassay cards often arises in the context of conducting a multiplex immunoassay. FIG. 2 depicts an exemplary multiplex immunoassay card 2' composed of a fibrous pad 4, a sample reservoir 6, a reagent pad 12, and three test strips 8a, 8b, and 8c. The flow of the sample through the fibrous pad 4 is in the direction of the arrow from the sample reservoir 6 toward the test strips 8a, 8b, 8c. The multiplex assay may be desirable when trying to determine the presence of multiple antigens from a single sample source. For example, in obstetrics, it may be desirable to perform an assay on blood to simultaneously determine blood type, Rh factor, and pregnancy. Therefore, a multiplex immunoassay card 2' may have a first test strip 8a with antibodies specific to blood type antigens, a second test strip 8b with antibodies specific to an Rh factor, and a third test strip 8c with antibodies receptive to antigens indicating pregnancy. A problem can arise in such multiplex assays in the circumstance wherein there is a high percentage of the antigen receptive to the first test strip 8a. In some instances, when a large quantity of antigen and reagent bind to the first test strip 8a, they actually block the flow of the sample beyond the first test strip 8a. In this circumstance, the other antigen-reagent pairs fail to reach the second test strip 8b or the third test strip 8c resulting in an inaccurate overall assay.

A fourth problem with the use of immunoassay cards 2 is the length of time required to complete an assay. The time for completion of an assay is directly related to the flow rate of a sample through the fibrous pad 4. This flow rate in turn directly depends on the viscosity of the sample and the wicking ability of the material used for the fibrous pad 4. Therefore, results of an assay may not be available for a period of time between several minutes to several hours depending upon the nature of the sample and of the fibrous pad 4. Also, the time to result is delayed because of a need to wait for the sample to reach the control strip 10 to insure that the immunoassay card has properly functioned.

Figure 3:
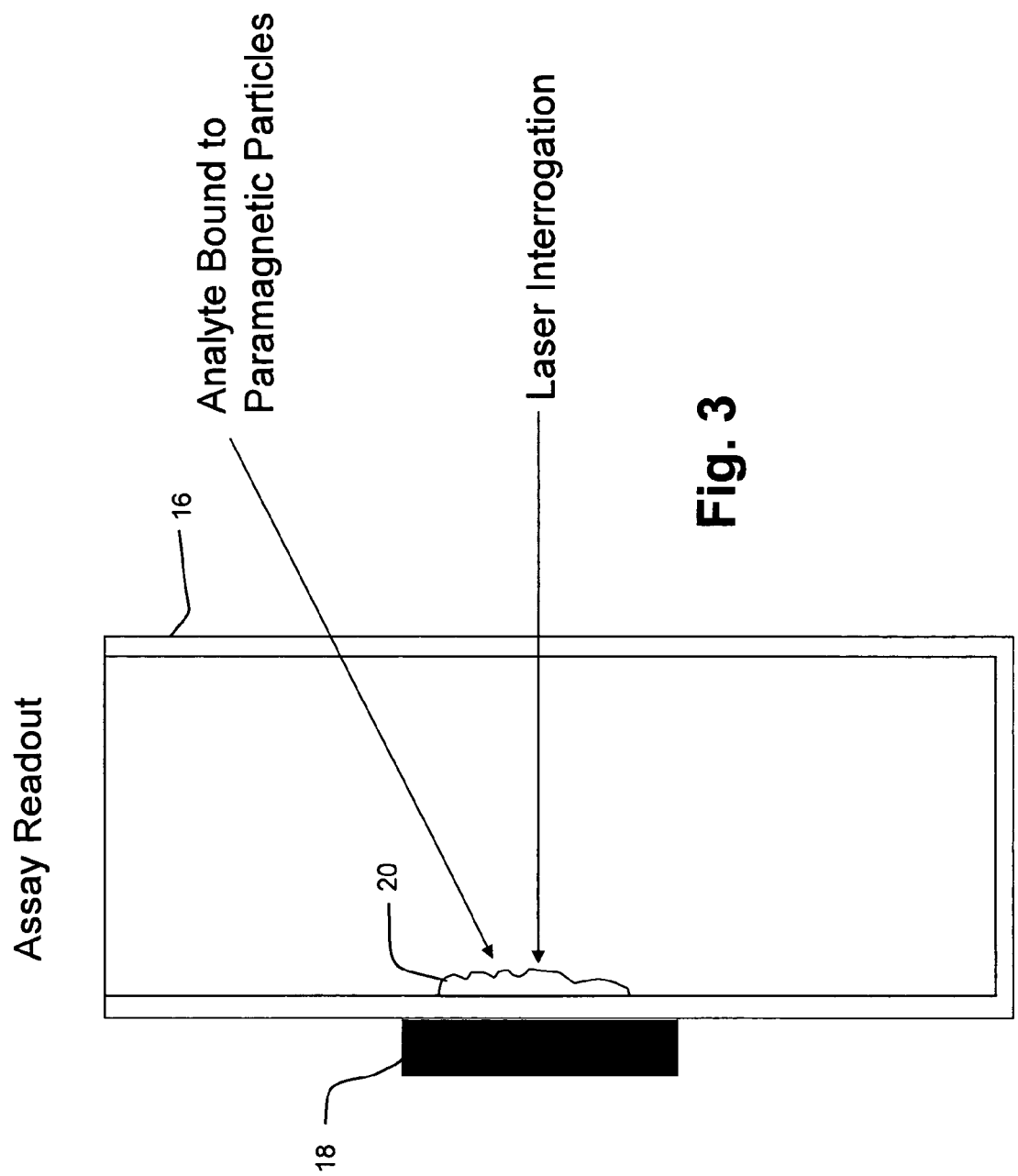
FIG. 3 is a schematic diagram of a Raman spectral assay system incorporating paramagnetic particles as reagents according to a generic embodiment of the invention.

The present invention is directed, in part, to systems and methods that overcome these significant limitations of current lateral flow immunoassay technology. FIG. 3 schematically represents a system that provides rapid spectral interrogation of a sample for the presence of a specific analyte. The assay is performed by analyzing the Raman spectrum of a specific sample for an indicator of the presence of the analyte. The indicator may be a spectrum signature of the analyte itself, or a spectrum signature of a tag that is designed to bind with the analyte.

A general spectral assay scheme according to the present invention is depicted in FIG. 3. A sample chamber 16 receives a liquid sample containing the analyte in suspension or solution. In addition to the analyte, paramagnetic particles and spectral enhancement particles are also suspended in the solution and are designed to bind with the analyte either individually or bind to each other while one or the other of the paramagnetic particles or the spectral enhancement particles additionally binds to the analyte. The spectral enhancement particles may either enhance the actual Raman spectral response of the analyte or act as a reporter to indicate the presence of the analyte. If the spectral enhancement particle acts as a reporter, a spectral flag compound with a known, strong Raman spectrum is bound to the surface of the metal nanoparticle.

It should be noted that when an analyte is described as binding with a paramagnetic particle or a spectral enhancement particle, in actuality tens, hundreds, thousands, or more of analytes (e.g., antigens, other proteins, or chemical compounds) may actually bind to a single spectral enhancement particle and/or paramagnetic particle. Thus, the figures presented in this specification are meant to be illustrative only of the binding event and not the number of particles and analytes involved in any particular binding event. Additionally, when a spectral enhancement particle or paramagnetic particle is described as being coated with a material, in actuality tens, hundreds, thousands, or more of discrete material components (e.g., antibodies or molecules) actually coat or are connected with a single spectral enhancement particle and/or paramagnetic particle.

A magnet 18 is positioned adjacent the sample chamber 16 and attracts the paramagnetic particles in the sample solution to form a condensation 20 of paramagnetic particles and any spectral enhancement particles and analyte bound thereto in a specific location within the sample chamber 16. This condensation 20 of particles and analytes can then be easily interrogated by a laser in order to perform a spectral analysis of the condensation through Raman scattering effects and thus determine the presence of an analyte.

The cross-sectional area of the laser beam used to interrogate the particle-analyte condensation 20 and create the Raman scattering effect is very small. The area of the beam must be small in order to produce the Raman spectrum. The area of the laser beam controls the width of the peaks in the Raman spectrum and, if the area of the beam is too large, the amount of information in the spectrum is diminished. However, if the analyte bound to the corresponding paramagnetic particles and spectrum enhancement particles were to remain dispersed in the sample solution, only a small portion of the sample solution could be interrogated by the laser beam. Thus, if the analyte remained dispersed, the spectral signal created might be very weak, or the presence of the analyte may be missed altogether. However, through the use of the magnet 18, the paramagnetic particles are attracted to collect or condense at a very discrete, localized spot adjacent to the magnet 18. Since the analyte and the spectral enhancement particles are attached to the paramagnetic particles, a high concentration of the analyte, if present, will be localized in an area adjacent to the magnet 18, can be completely interrogated by the laser, and will thereby produce a strong Raman spectrum.

The assay performed can either be a direct assay or a competitive assay. In a competitive assay, a second spectral enhancement particle and analyte coupling may be added to the reaction to compete with any antigen in the sample (if any) for binding with the paramagnetic particle. This replacement effects a change in the Raman spectral response because of the second spectral enhancement particle, thus indicating the presence of analyte in the sample.

Figure 4:
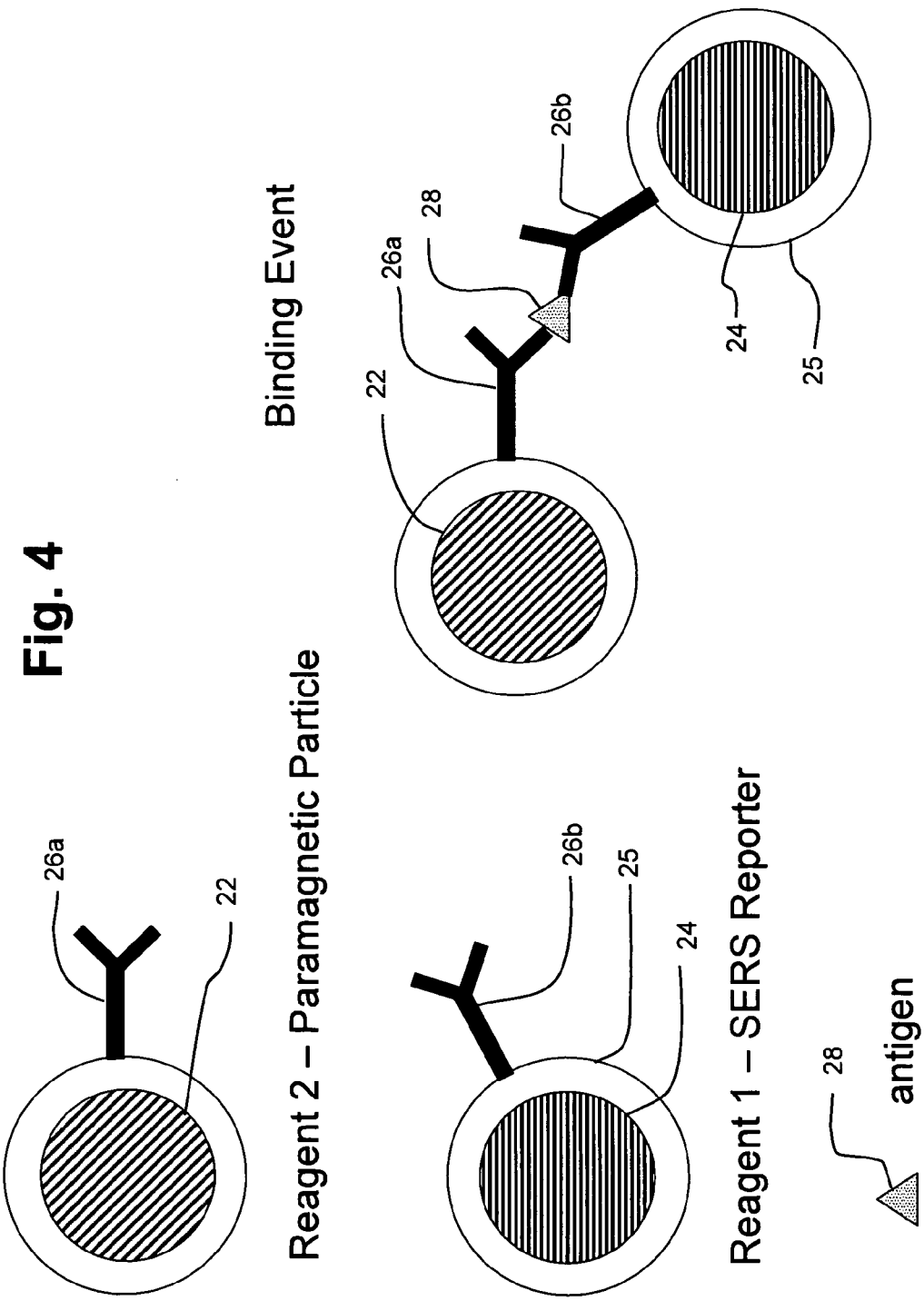
FIG. 4 is a schematic diagram of spectral enhancement particles and paramagnetic particles used as reagents to identify an antigen in assays, and a binding event between the particles and antigen according to the present invention.

FIG. 4 depicts a basic immunoassay configuration used in the present invention. The assay consists of two types of reagents that are configured to interact with the antigen 28 of interest. The first reagent is a paramagnetic particle 22 and the second reagent is a spectral enhancement particle 24. Exemplary paramagnetic particles may be nanoscale crystals of spinel iron oxides. Exemplary spectral enhancement particles may be colloidal nanoscale particles of silver, gold, or copper. The paramagnetic particles 22 are coated or otherwise bound to a plurality of antibodies 26a that are receptors for the antigen 28. The spectral enhancement particles 24 are similarly coated or otherwise bound to a plurality of antibodies 26b with receptors for the antigen 28 of interest. The coating process, its ability to be an internal standard for a detection process, its ability to protect a surface, and its affinity for an analyte are discussed in U.S. Pat. No. 5,693,152, which is hereby incorporated by reference in its entirety. Exemplary methods for binding antibodies to colloidal particles are described in U.S. Pat. No. 6,770,488, which is also hereby incorporated herein by reference in its entirety. In solution with the antigen 28, one of the antibodies 26a on the paramagnetic particle 22 binds to a site on the antigen 28. Similarly, one of the antibodies 26b on the spectral enhancement particle 24 binds to a different site on the antigen 28. The two antibodies 26a, 26b may be monoclonal antibodies and thereby bind to the same type of site on the antigens 28. Alternatively, the antibodies 26a, 26b may be different monoclonal antibodies or polyclonal antibodies and thereby bind to different sites, or epitopes, on the antigens 28. Thus, the antigen 28, which is the analyte in question, creates a coupling of the spectral enhancement particle 24 with the paramagnetic particle 22, as shown in FIG. 4.

Figure 5:
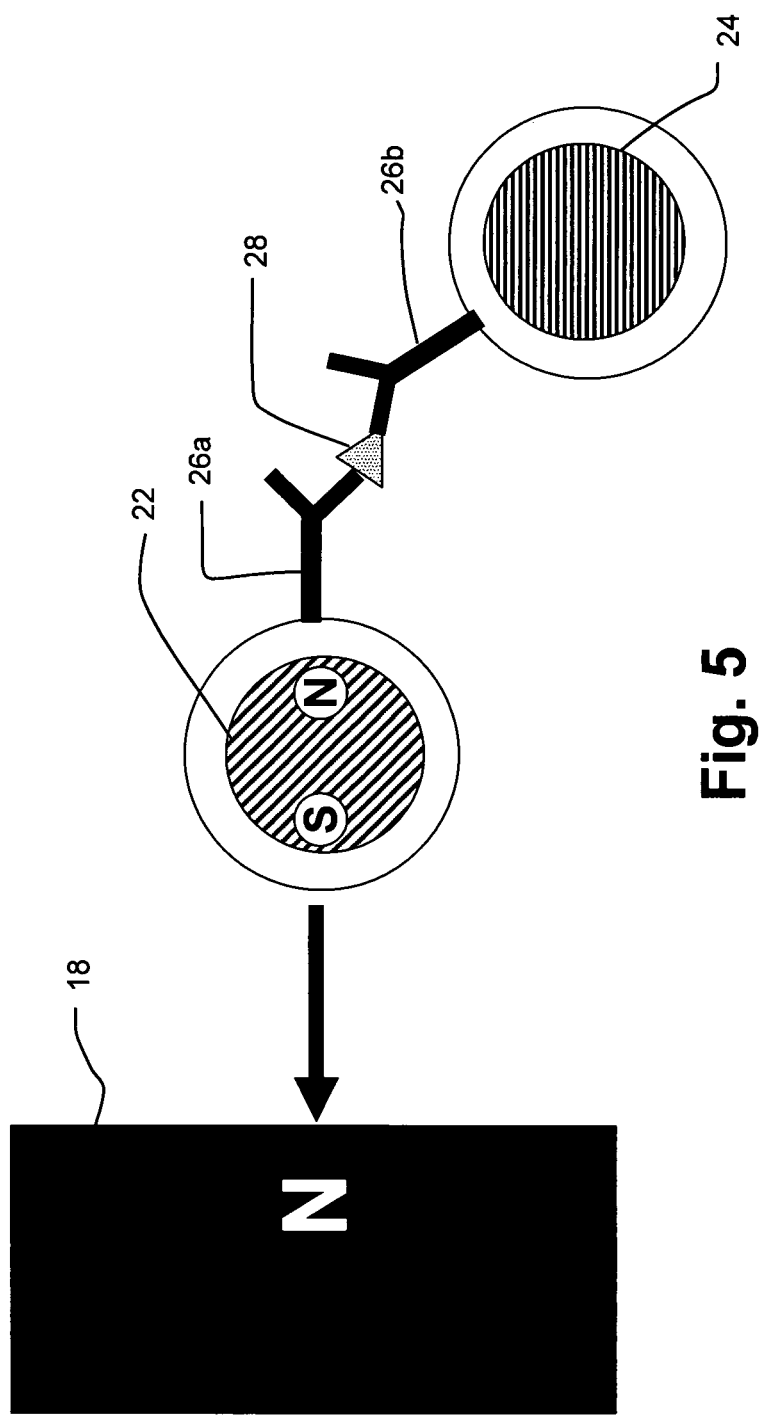
FIG. 5 is a schematic diagram depicting the reaction of a paramagnetic particle in a magnetic field. The influence of the magnetic field on the paramagnetic particle is not impacted by the binding event with the antigen and the spectral enhancement particle.

As shown in FIG. 5, the paramagnetic particle 22 becomes polarized in a magnetic field and is thus attracted to the magnet 18. Since the spectral enhancement particle 24 is coupled to the paramagnetic particle 22 through the antigen 28, the entire particle grouping can be concentrated by a magnetic field, along with similar particle groupings, at a single location in the sample chamber 16 (see FIG. 3). Further, because the particle combinations are concentrated adjacent the magnet 18, the particle combinations can be condensed or otherwise taken out of the sample solution by the magnet 18. It should be noted that due to the relative size of the paramagnetic particles 22 and surface enhancement particles 24 on the one hand and the antigens 28 on the other, that there may be multiple bonds between a single pair of a paramagnetic particle 22 and a spectral enhancement particle 24. Thus, a plurality of antigens 28 may bind to a single pair of paramagnetic particle 22 and spectral enhancement particle 24 via a plurality of antibodies 26a, 26b bound to the outer surfaces of each of the paramagnetic particle 22 and spectral enhancement particle 24, respectively.

Figure 6:
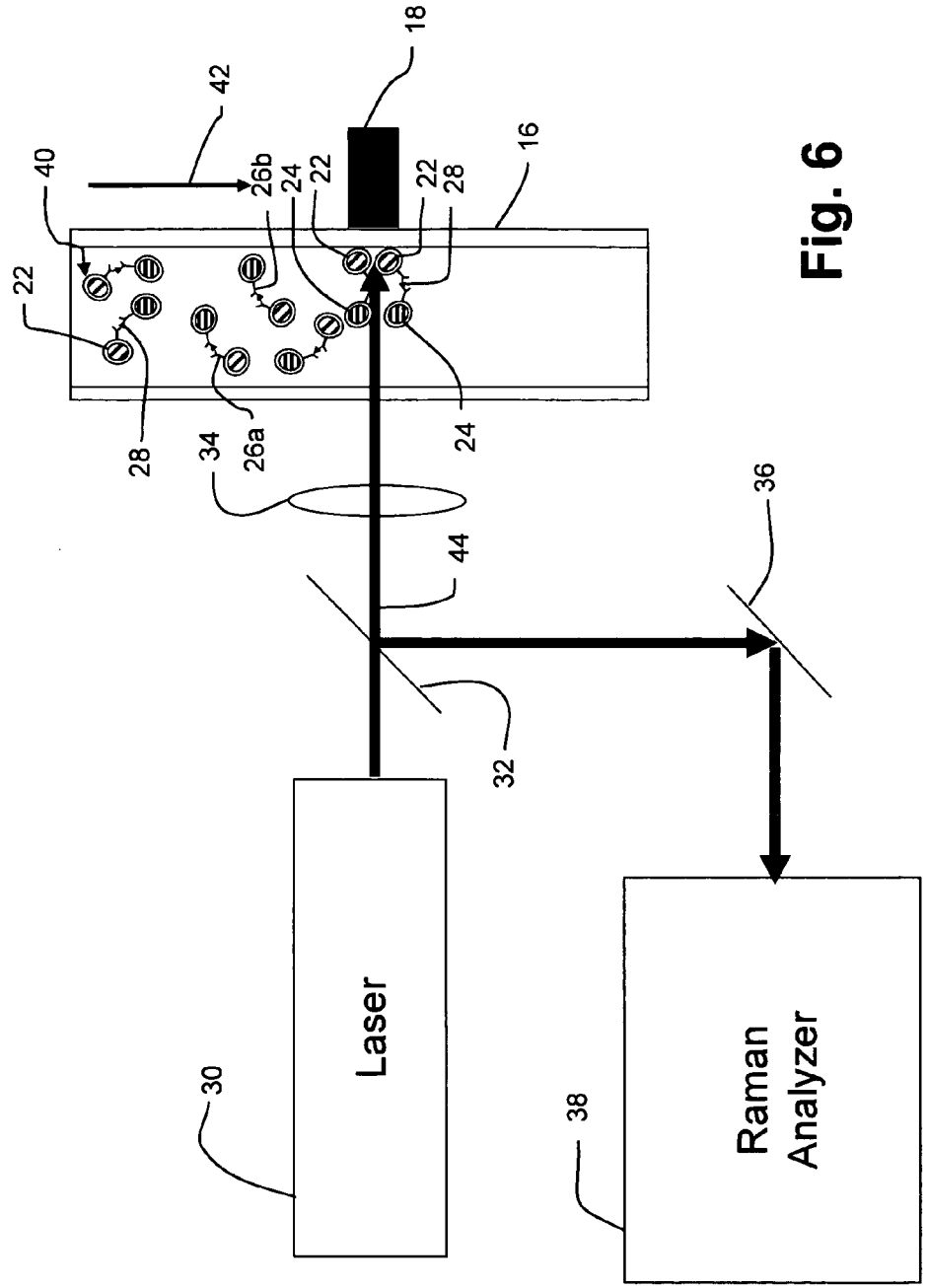
FIG. 6 is a schematic diagram of an exemplary Raman spectroscopy immunoassay system wherein paramagnetic particles are used to localize the antigen for laser interrogation. This exemplary assay is positive for a desired antigen.

FIG. 6 depicts a paramagnetic immunoassay analyzer according to one embodiment of the present invention. The analyzer comprises of a glass sample chamber 16 in which the sample in solution is introduced. A magnet 18 is positioned along one wall of the sample chamber 16 directly across from a laser 30. A beam splitter 32 and lens 34 are situated between the laser 30 and the sample chamber 16. A mirror 36 is positioned symmetric with the beam splitter 32 and orthogonal to the beam of light focused by the laser 30.

A Raman analyzer 38 collects light reflected by the mirror 36. Traditionally, Raman spectroscopy might be considered to have low sensitivity, but technology improvements enable the signal to be enhanced by million to over a trillion orders of magnitude. The basic design uses a diffractive spectrometer coupled with epi-illumination and diode laser excitation.

As shown in FIG. 6, a plurality of analyte couplings 40, each comprising a paramagnetic particle 22 and a surface enhancement particle 24 joined via antibodies 26a, 26b to an antigen 28 are suspended or dissolved within the sample solution. The magnet 18 attracts the paramagnetic particles 22 in each of the analyte couplings 40 and creates a concentration of the analyte couplings 40 adjacent the position of the magnet 18 within the sample chamber 16. Because of the attraction between the magnet 18 and the paramagnetic particles 22, a flow of the analyte couplings 40 is created within the sample chamber 16 in a direction as indicated by the arrow 42. Thus a large concentration of analyte couplings 40 can be quickly achieved adjacent the magnet 18. Further, because the analyte couplings 40 are concentrated in a single location, they can easily be interrogated by the laser beam 44 generated by the laser 30.

A portion of the laser beam 44 is deflected by the beam splitter 32 and travels to the mirror 36 and ultimately to the Raman analyzer 48. The remainder of the laser beam 44 passes through the beam splitter 32 and is focused by the lens 34 to interrogate the condensate of analyte couplings 40 adjacent the magnet 18. Some of the light in the laser beam 44 will be scattered by the analyte couplings 40 and will exhibit a Raman scattering effect. The Raman scattering will be amplified by the presence of the spectral enhancement particles 24. The Raman scattered light will be reflected to the beam splitter 32, transmitted to the mirror 36, and ultimately to the Raman analyzer 38 where a detection of the instant light and the detection of the Raman scattered light and filtering of the laser occurs.

Figure 7:
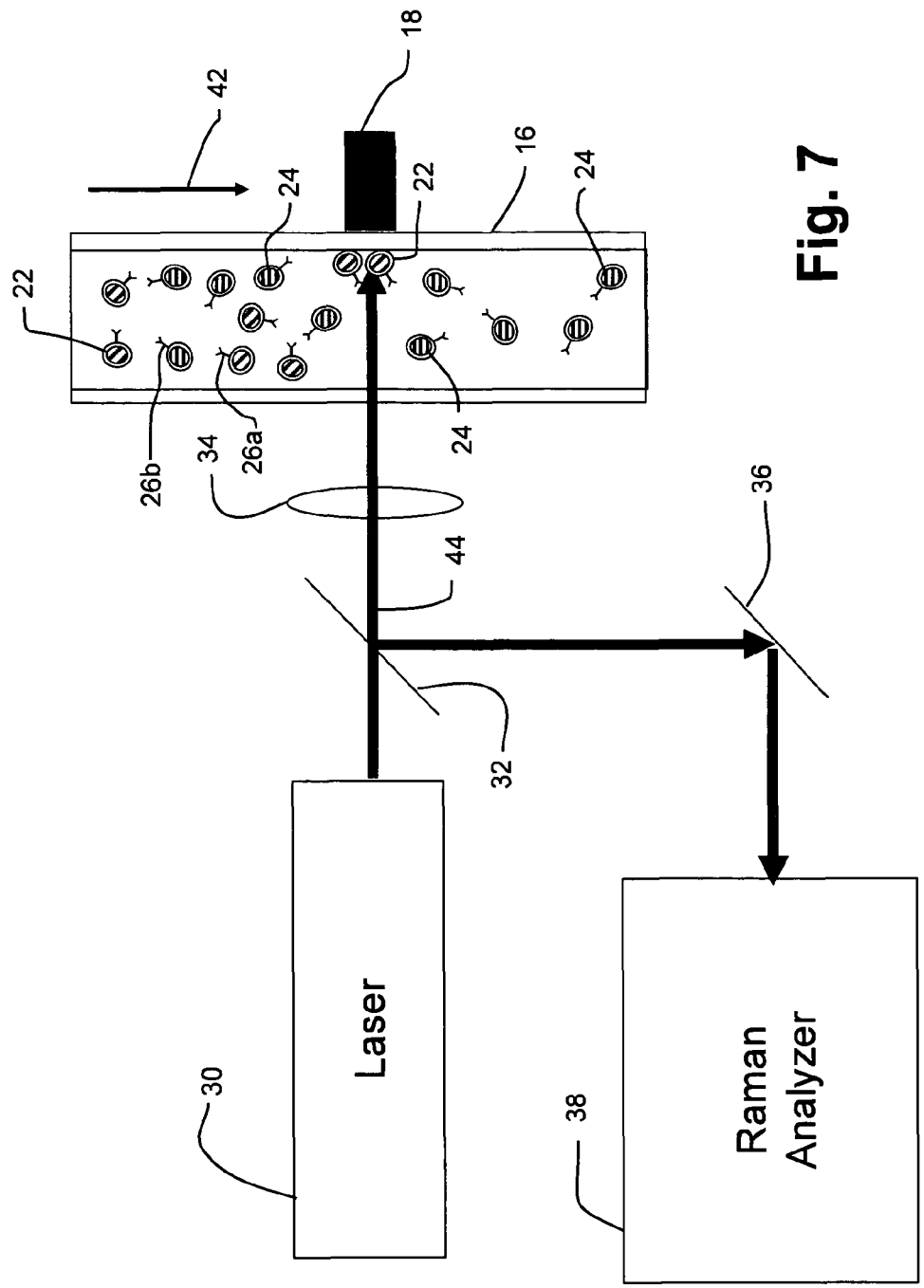
FIG. 7 is a schematic diagram of the immunoassay system of FIG. 6 indicating a negative result for a desired antigen.

In particular because of the presence of the spectral enhancement particles 24 in each of the analyte couplings 40, the Raman effect will be significantly enhanced and a strong signal will be recorded by the Raman analyzer 38. It should be noted that in this particularly configuration, the spectral enhancement particles 24 are acting as reporters for the presence of the antigen 28. This means that the spectrum signature reported by the Raman analyzer will not be the spectrum signature of the antigen 28 itself, but rather the spectrum signature of a spectral flag compound 25 also bound to the spectral enhancement particle 24. The presence of the antigen 28 is thereby determined indirectly. If the antigen 28 were not present in the sample solution, there would be no binding event between any of the paramagnetic particles 22 and the spectral enhancement particles 24. Thus, although the paramagnetic particles 22 would be attracted to the magnet 18, the spectral enhancement particles 24 would not be attached to the paramagnetic particles 22 and would not be concentrated adjacent the magnet 18, but would instead be freely floating within the sample solution. This is the precise situation shown in FIG. 7 wherein a negative assay for a desired analyte is reported because there is no antigen within the sample chamber 16 to bind the surface spectral enhancement particles 24 to the paramagnetic particles 22. Note that while the paramagnetic particles 22 are attracted by the magnet 18, the spectral enhancement particles 24 pass through the magnetic field of the magnet 18 because of the induced flow 42.

Figure 8:
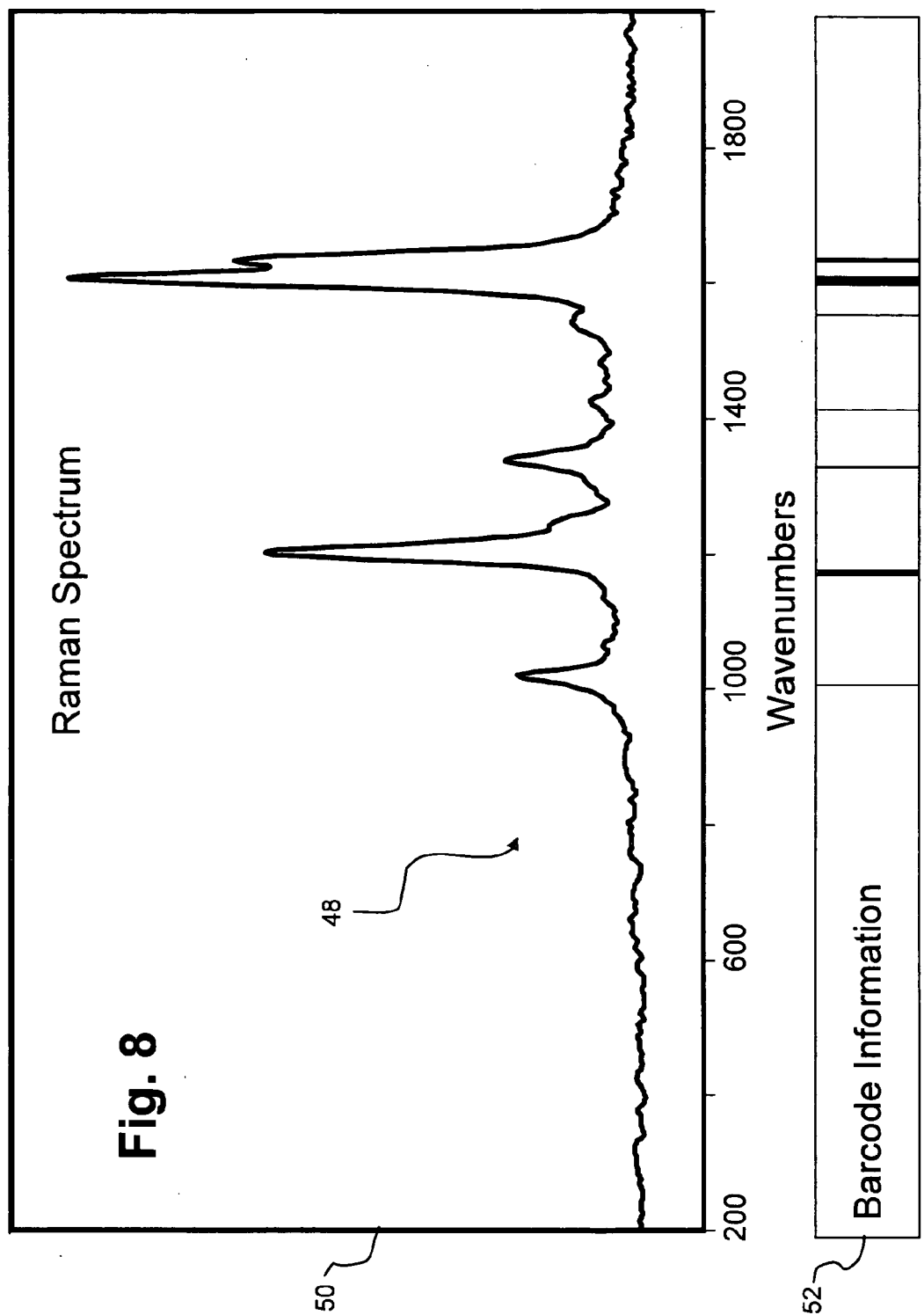
FIG. 8 is a schematic diagram interpolating a Raman spectrum as a barcode for analyte identification in an assay.

FIG. 8 represents a novel way of thinking about Raman spectra. A Raman spectrum 48 of a particular analyte is depicted in the graph 50. Traditionally, Raman spectra have been analyzed for line shapes, line positions, and line intensities. However in the context of the present invention, Raman spectra can be used simply as markers for assays. A simple but accurate way to think about a Raman spectrum is as a barcode 52. The position and thickness of each line of the barcode 52 corresponds to the position and intensity of the Raman spectrum 48 at a particular wave number. The general theory behind Raman spectral analysis is that each molecule will absorb and reflect any combination of wavelengths of light and thus a unique Raman spectrum can be associated with each particular molecule. Therefore, when a Raman spectrum 48 is translated into a barcode 52, a unique barcode 52 can be correlated to each molecule of interest as an analyte.

Figure 9:
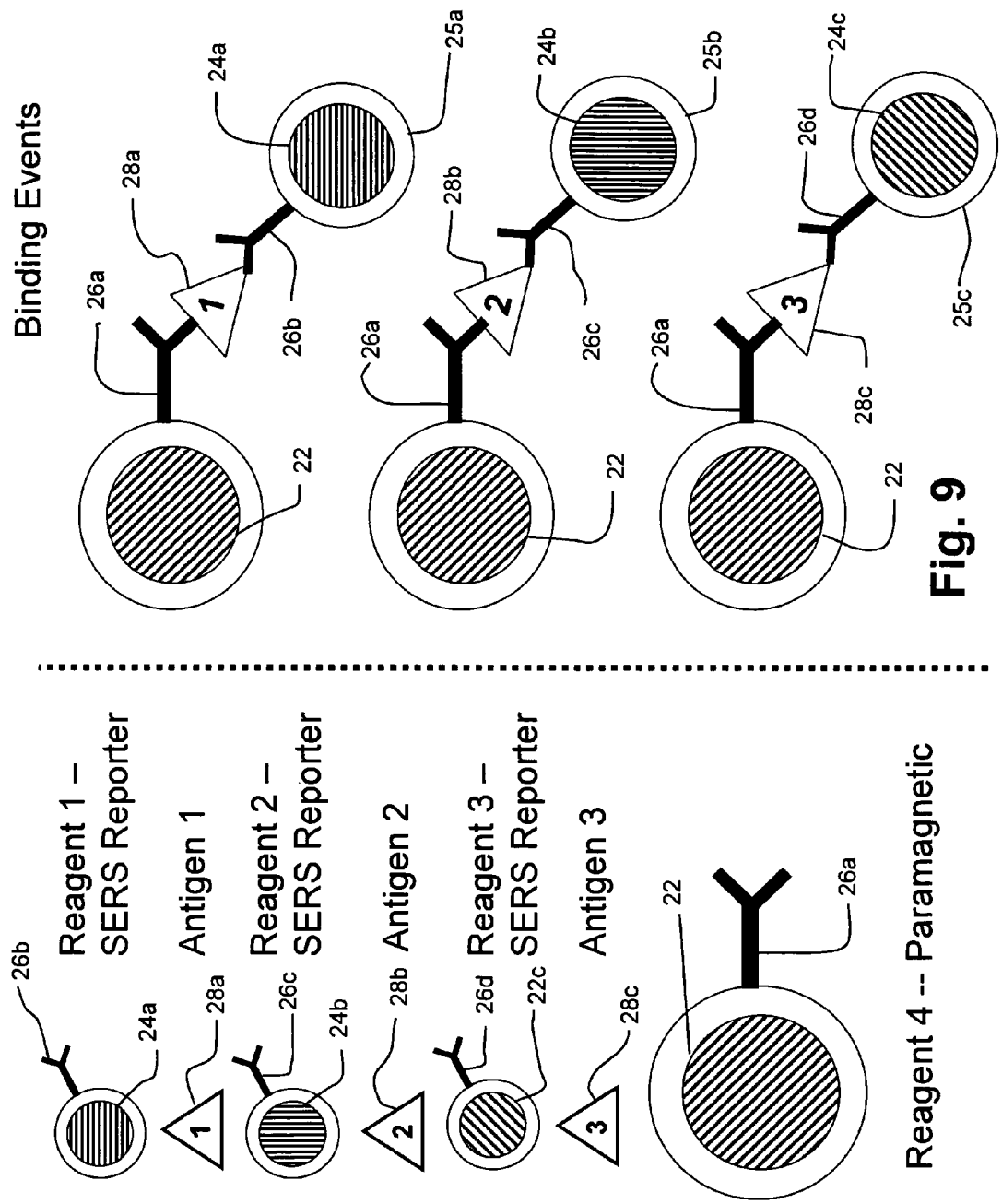
FIG. 9 is a schematic diagram of spectral enhancement particles and paramagnetic particles used as reagents to identify multiple antigens in a single multiplex assay. The diagram shows binding events between a single type of paramagnetic particle, multiple types of spectral enhancement particles receptive to different antigens, and several unique antigens according to the present invention.

This concept of translation of Raman spectra to unique barcodes lends itself to a novel methodology to multiplex assays to measure a large number of analytes in a single sample. FIG. 9 is an illustration of the components used in a multiplex assay. In this exemplary embodiment, the goal of the assay is to determine the presence of up to three different antigens 28a, 28b, 28c in a sample. Returning to the prior blood test example, the antigens could be for blood type, Rh factor, and pregnancy indicative proteins. In this embodiment, three separate SERS active reagents are used. Each reagent is formed by binding each of three different spectral enhancement particles 24a, 24b, 24c to one of three different antibodies 26b, 26c, 26d, respectively. Each antibody 26b, 26c, 26d has a different receptor specific to one of the three antigens 28a, 28b, 28c. Each of the different spectral enhancement particles 24a, 24b, 24c is additionally coated with a unique spectral flag compound 25a, 25b, 25c that provides unique spectral signatures when the sample is analyzed. The spectral flag compounds 25 are chosen to be formulations that produce strong Raman scattering effects and therefore will generate strong Raman spectra for analysis.

Figure 10:
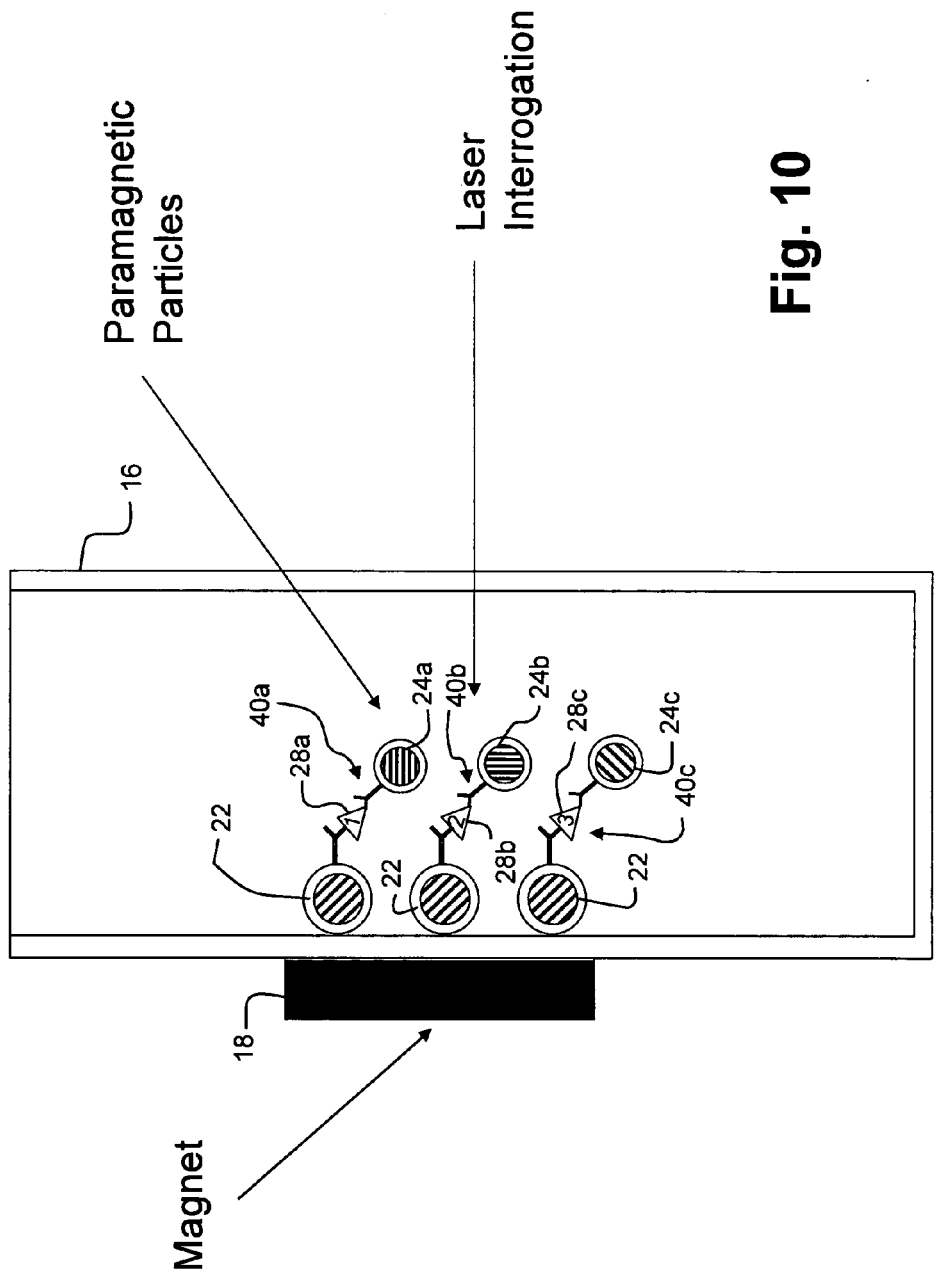
FIG. 10 is a schematic diagram of an exemplary Raman spectroscopy multiplex immunoassay wherein paramagnetic particles are used to localize multiple antigens for laser interrogation.

A fourth reagent is formed of paramagnetic particles 22 coated with antibodies 26a with a receptor common to each of the antigens 28a, 28b, 28c of interest. In an alternative embodiment, the paramagnetic particles may have a set of unique antibodies with respective receptors having an affinity for only a subset (e.g., one or two) of the antigens 28a, 28b, 28c. As shown in FIG. 10, a multiplex assay for one or more of the several antigens 28a, 28b, 28c can be performed simultaneously within the sample chamber 16. As before, the paramagnetic particles 22 are drawn to the magnet 18 in the sample chamber 16 (see FIG. 10). When a paramagnetic particle 22 is linked to a respective one of the spectral enhancement particles 24a, 24b, 24c through a corresponding antigen 28a, 28b, 28c, the entire analyte coupling 40a, 40b, 40c is positioned adjacent the magnet 18.

Figure 11:
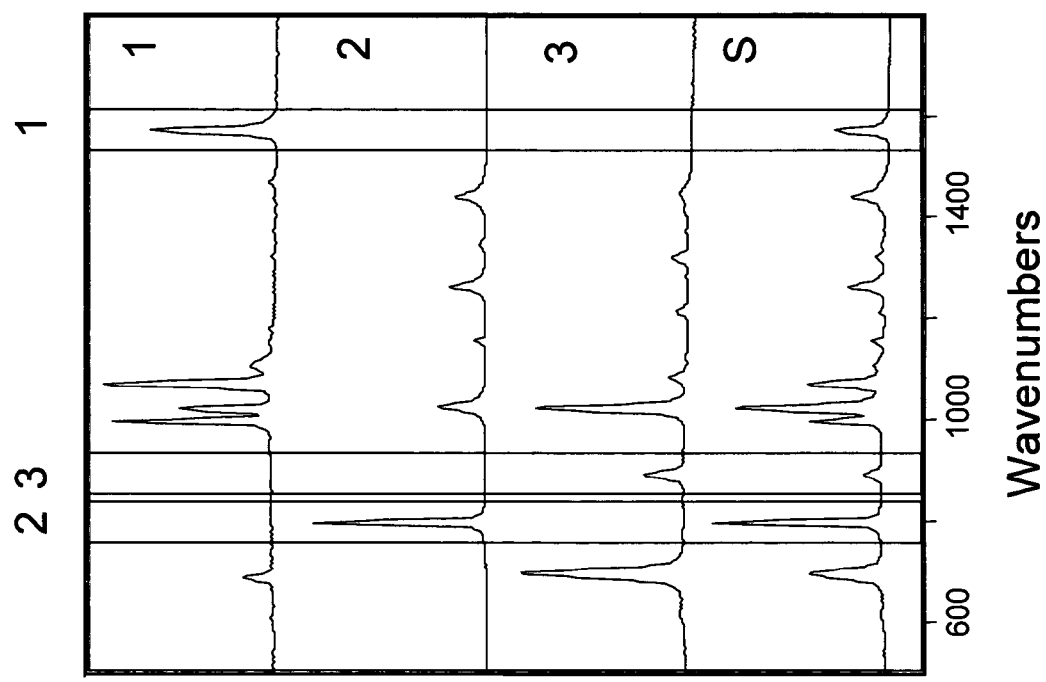
FIG. 11 is exemplary Raman spectra from a multiplex assay.

The assay system of FIG. 10 suggests a significant improvement over the prior art laminar flow assay described above. As noted, performing a multiplex assay on a laminar flow substrate often leads to inaccurate results, primarily false negatives for certain antigens, because the first test strip clogs and prevents flow to the later test strips. This problem is avoided by the present invention as there is no possibility for blocked movement of the antigens in the sample solution. Because Raman spectroscopy is capable of reading multiple spectra simultaneously, a multiplexed assay of the sample can be generated as shown in FIG. 11. Spectra 1, 2, and 3 represent exemplary spectra of the spectral enhancement particle reporters 24a, 24b, 24c. Spectrum S is the sum of the three reporter spectra and represents the spectral output of a Raman spectral analyzer. As indicated by the bands superimposed across the spectra, different wavelengths unique to each of the reporters can also be identified in the multiplexed spectrum S. The three bands are analogous to a barcode that can be easily read to indirectly identify the presence of an antigen of interest. Recall, there will be no indication of the presence of any particular reporter unless the corresponding antigen is present in the sample to link the spectral enhancement particle to the paramagnetic particle.

Figure 12:
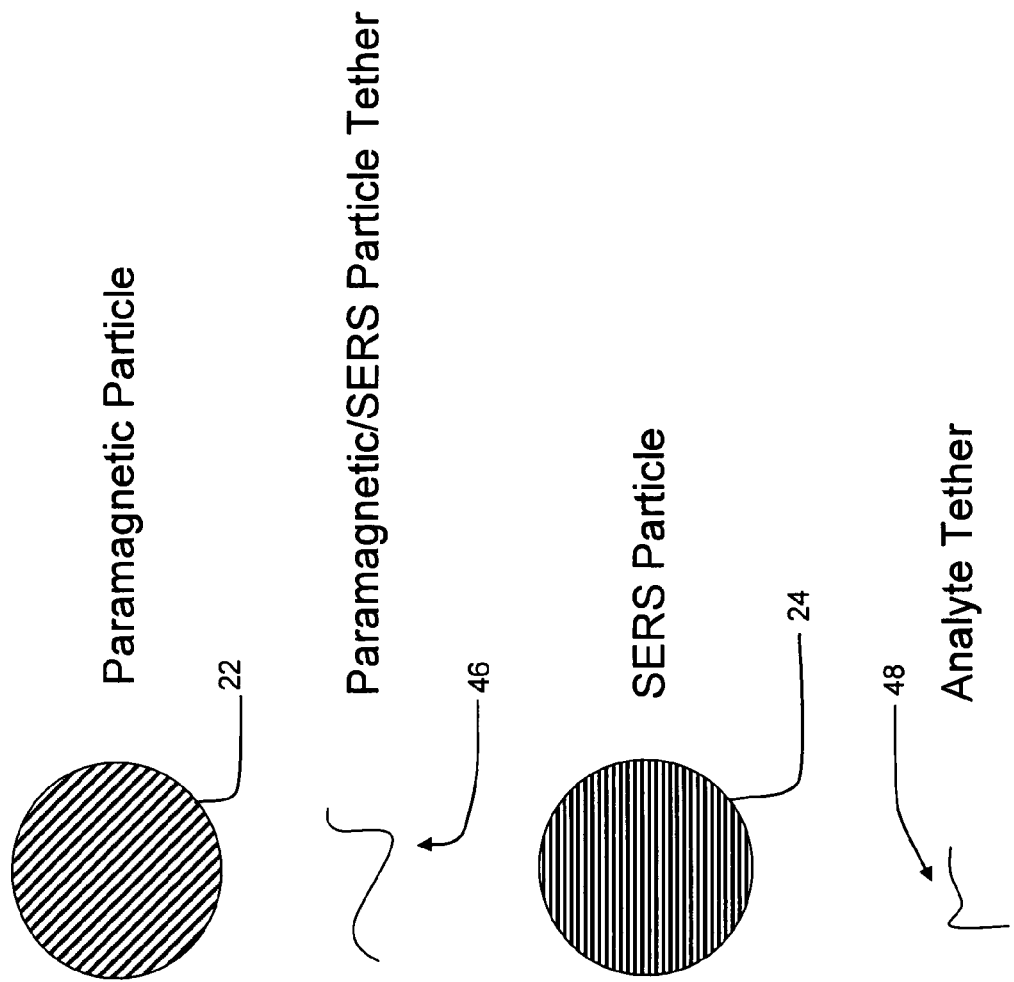
FIG. 12 is a schematic diagram of paramagnetic particles, spectral enhancement particles, and chemical tethers for binding the particles to each other and to an analyte according to another embodiment of the invention.
Figure 13:
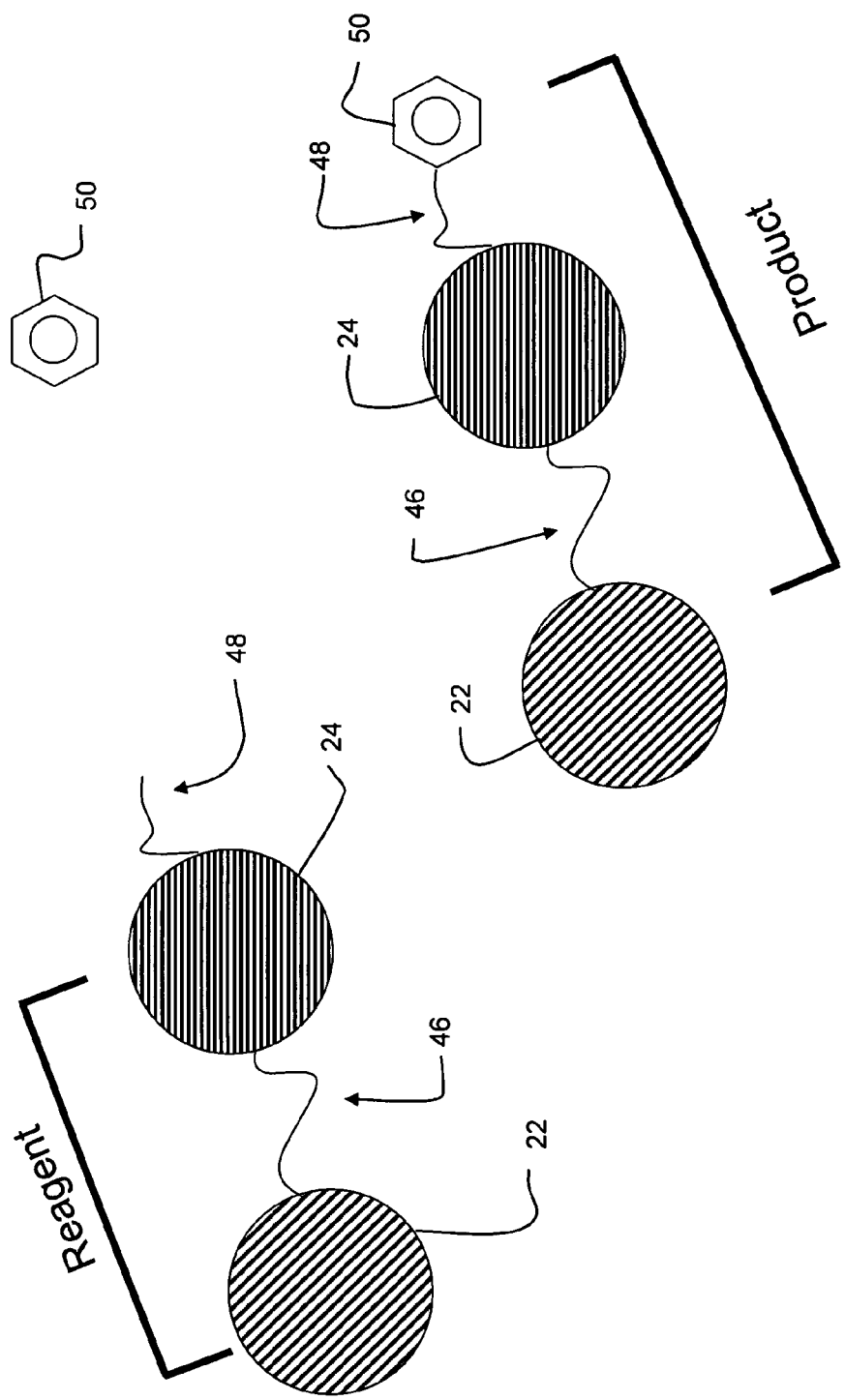
FIG. 13 is a schematic diagram of first, a reagent formed of the particles and tethers of FIG. 12, and second, a product formed of the reagent bound via a tether to an analyte.

An analogous approach for chemical analysis using paramagnetic particles for analyte separation and concentration is depicted in FIGS. 12-20. As shown in FIGS. 12 and 13, paramagnetic particles 22 are chemically tethered by a particle tether 46 compound to spectral enhancement particles 24, for example silver nanoparticles. The spectral enhancement particles 24 are additionally bound to the analytes 50 via an analyte tether 48 compound. The chemistries of the iron paramagnetic and silver particles differ sufficiently that a bifunctional tether can be easily designed. Exemplary methods for creating tethers to bind analytes to colloidal particles are described in U.S. Pat. No. 6,558,956, which is hereby incorporated herein by reference in its entirety. Iron chemistry is rich in bidentate aromatic nitrogen ligands which include classic ligands such as bipyridines and 1,10-phenanthroline. Silver, on the other hand, is highly polarizable and will covalently bind with sulfur compounds. As illustrated in FIG. 13, a pair of a paramagnetic particle and a spectral enhancement particle can be tethered together with a bifunctional molecule with a ferriphilic end and an argentiphilic functional group.

Figure 14:
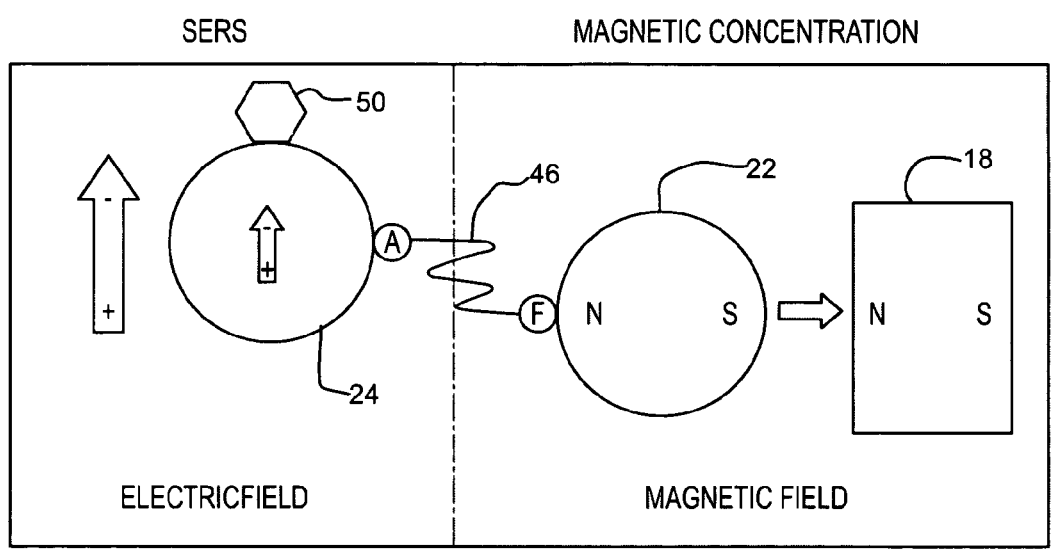
FIG. 14 is a schematic diagram of the effect of an electric field and a magnetic field on the reagent/analyte product of FIG. 13.

Once the tethering has occurred, an external magnetic field can instantaneously magnetize the paramagnetic particles 22 causing the paramagnetic particles 22 to act as an nanoengine to move the spectral enhancement particles 24 and attached analytes 50. In FIG. 14 the spectral enhancement particle 24 is seen polarized by the optical electric field of the laser with its induced dipole oriented in the direction of the electric field. An analyte 50 is shown tethered to the spectral enhancement particle. In principle, the electric field of the laser light will repel the spectral enhancement particle 24. This is the exact opposite of optical trapping and stems from the property of a negative dielectric constant of the spectral enhancement particle 24 that is essential for the SERS effect. By tethering the spectral enhancement particles 24 to the paramagnetic particles 22, this deleterious repulsion will not occur because the magnetic trap counters the electric field of the laser beam.

Figure 15:
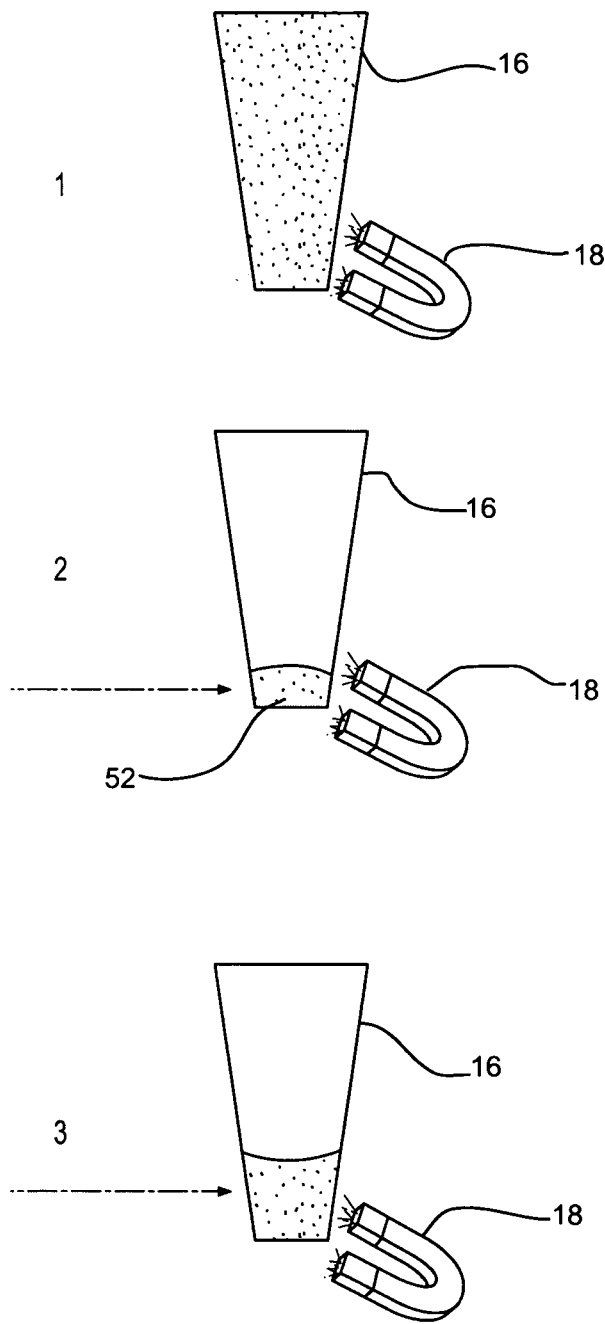
FIG. 15 is a schematic diagram of steps of concentrating an analyte bound to paramagnetic particles using a magnetic field according to the present invention.

In one embodiment depicted schematically in FIG. 15 powerful rare-earth magnets can be used to concentrate the tethered particles 52 in a solution by acting on the paramagnetic particles. In scene (1) of FIG. 15, the magnet 18 is just beginning to concentrate the tethered particles in the lower portion of the sample chamber 16. In scene (2) of FIG. 15 the tethered particles are formed into a highly concentrated "ball" of particles. Raman analysis performed on this ball has the advantage of very high concentration of spectral enhancement particles attached to the paramagnetic particle engines. However, practically, it may suffer from laser induced photobleaching during the acquisition. In scene (3) of FIG. 15, the "inactive" sample matrix has been removed from the sample chamber and replaced with pure buffer into which the concentrated tethered particles 52 may be returned to solution. This dissolution can eliminate interferences and provides a liquid-like sample to increase the Brownian motion and constantly reintroduce fresh tethered particles 52 into the laser beam for analysis. The formation of solid material followed by reconstitution leads to signal amplification. For example, if a low density solution of silver nanoparticles tethered to paramagnetic particles interrogate a 1 mL sample and a magnetic field concentrates the tethered particles to a 10 μL volume, then a 100-fold signal enhancement is achieved.

Figure 16:
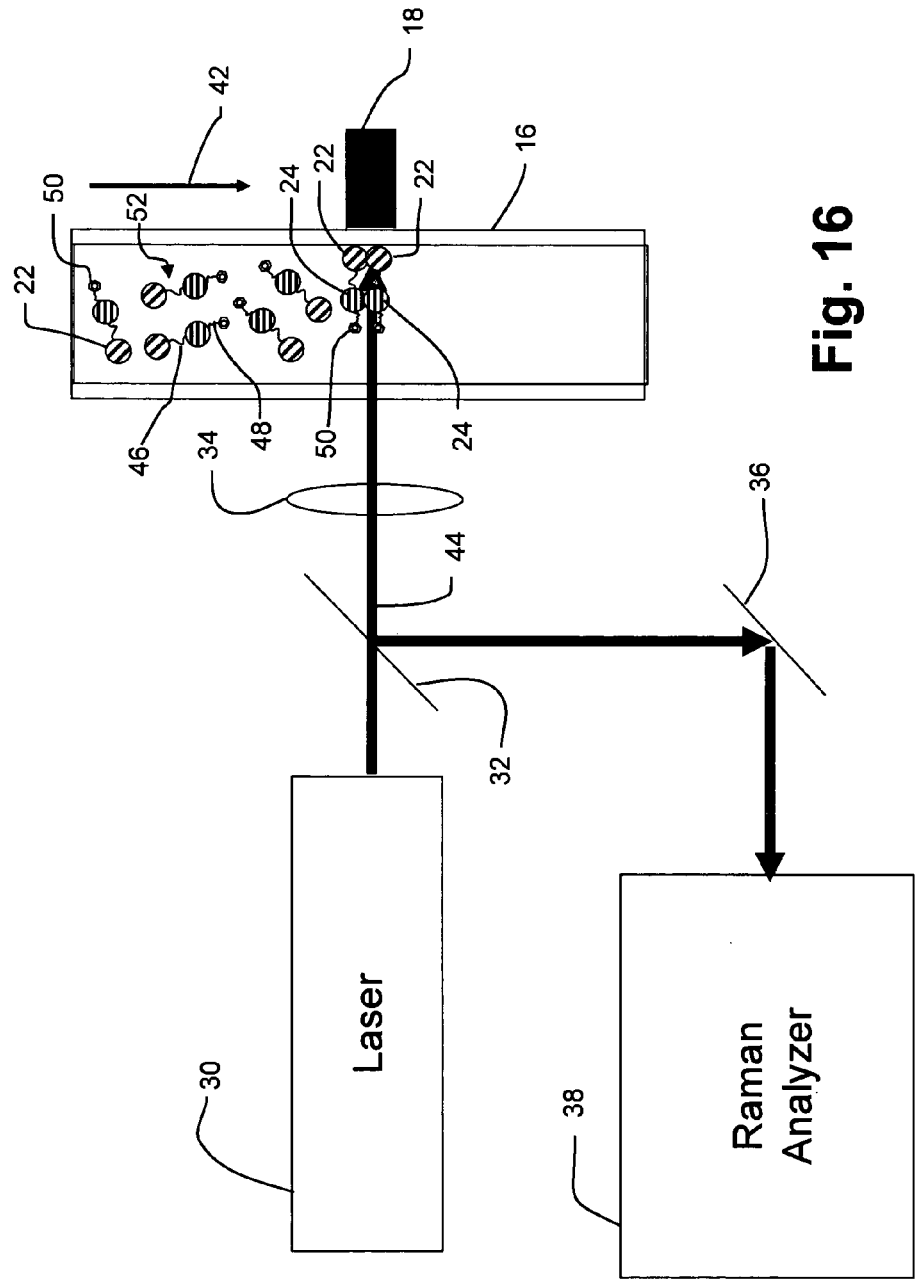
FIG. 16 is a schematic diagram of an exemplary Raman spectroscopy chemical assay system wherein paramagnetic particles are used to localize the analyte for laser interrogation. This exemplary assay is positive for a desired analyte.

FIG. 16 depicts a paramagnetic chemical assay analyzer according to one embodiment of the present invention. Similar to the immunoassay analyzer described above, the analyzer comprises a glass sample chamber 16 in which the sample in solution is introduced. A magnet 18 is positioned along one wall of the sample chamber 16 directly across from a laser 30. A beam splitter 32 and lens 34 are situated between the laser 30 and the sample chamber 16. A mirror 36 is positioned symmetric with the beam splitter 32 and orthogonal to the beam of light focused by the laser 30. A Raman analyzer 38 collects light reflected by the mirror 36.

As shown in FIG. 16, a plurality of tethered particles 52, each comprising a paramagnetic particle 22 and a surface enhancement particle 24 joined via a particle tether 46 and an analyte 50 joined to the surface enhancement particle via an analyte tether 48 are suspended or dissolved within the sample solution. The magnet 18 attracts the paramagnetic particles 22 in each of the tethered particles 52 and creates a concentration of the tethered particles 52 adjacent the position of the magnet 18 within the sample chamber 16. Because of the attraction between the magnet 18 and the paramagnetic particles 22, a flow of the tethered particles 52 is created within the sample chamber 16 in a direction as indicated by the arrow 42. Thus a large concentration of tethered particles 52 can be quickly achieved adjacent the magnet 18. Further, because the tethered particles 52 are concentrated in a single location, the attached analyte 50 can easily be interrogated by the laser beam 44 generated by the laser 30. This is a significant improvement in the assay as conventional Raman spectroscopy assays have no ability to align the analyte in solution with the laser beam.

A portion of the laser beam 44 is deflected by the beam splitter 32 and travels to the mirror 36 and ultimately to the Raman analyzer 48. The remainder of the laser beam 44 passes through the beam splitter 32 and is focused by the lens 34 to interrogate the condensate of tethered particles 52 adjacent the magnet 18. Some of the light in the laser beam 44 will be scattered by the tethered particles 52 and will exhibit a Raman scattering effect. The Raman scattering will be amplified by the presence of the spectral enhancement particles 24. The Raman scattered light will be reflected to the beam splitter 32, transmitted to the mirror 36, and ultimately to the Raman analyzer 38 where a detection of the instant light and the detection of the Raman scattered light and filtering of the laser occurs. In particular because of the presence of the spectral enhancement particles 24 in each of the tethered particles 52, the Raman effect will be significantly enhanced and a strong signature of the analyte 50 will be recorded by the Raman analyzer 38.

Figure 17:
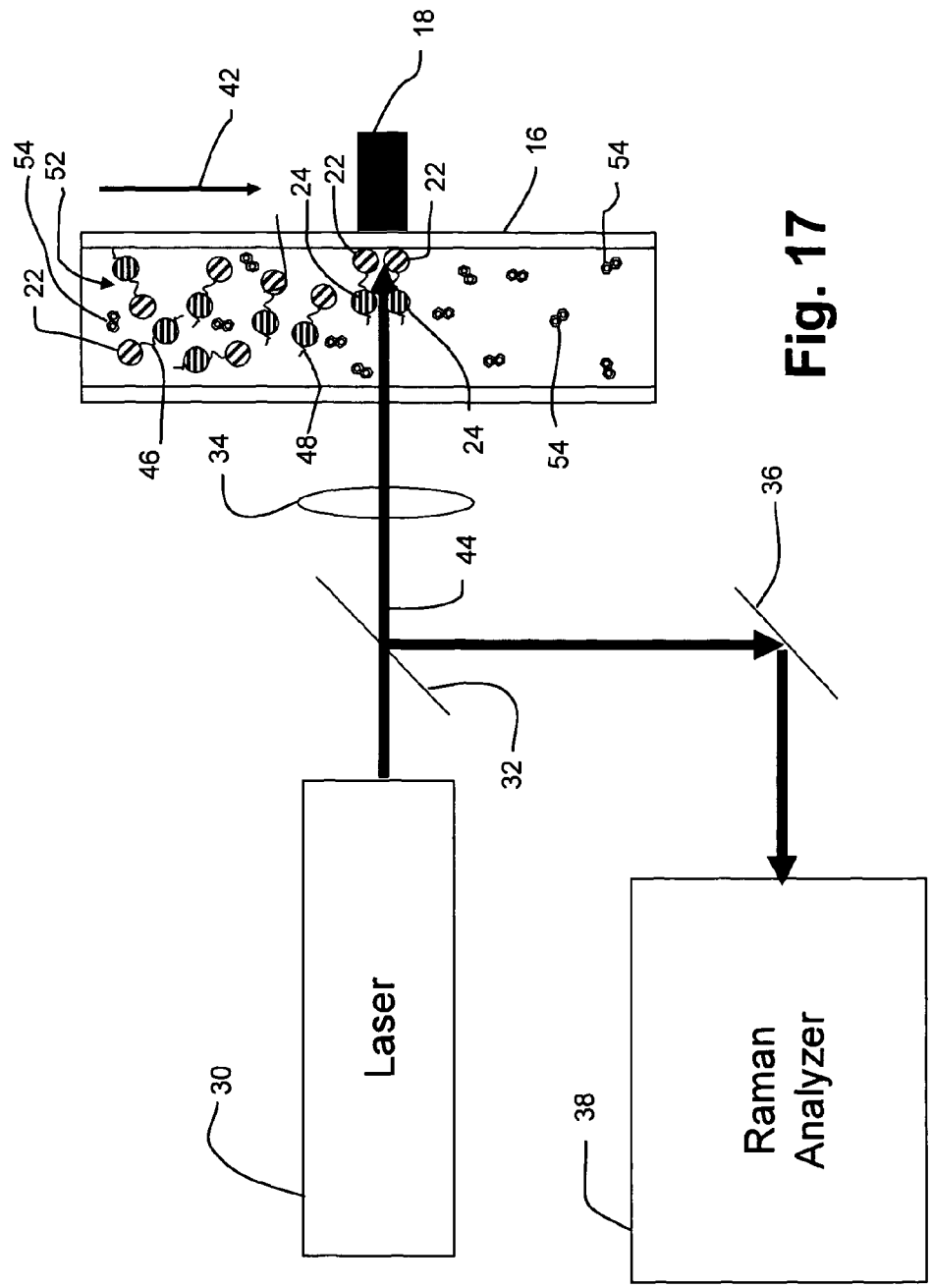
FIG. 17 is a schematic diagram of the immunoassay system of FIG. 16 indicating a negative result for a desired analyte.

However, if the desired analyte is not present in the sample solution, the Raman spectral assay will be negative as shown in FIG. 17. While the paramagnetic particles 22 and the spectral enhancement particles 24 are still tethered together and the paramagnetic particles 22 are attracted to the magnet 18, no analyte is attached to the spectral enhancement particles 24 to provide a Raman spectrum. Note that while the paramagnetic particles 22 are attracted by the magnet 18, other, untargeted analytes 54 merely pass through the magnetic field of the magnet 18 because of the induced flow 42.

Figure 18:
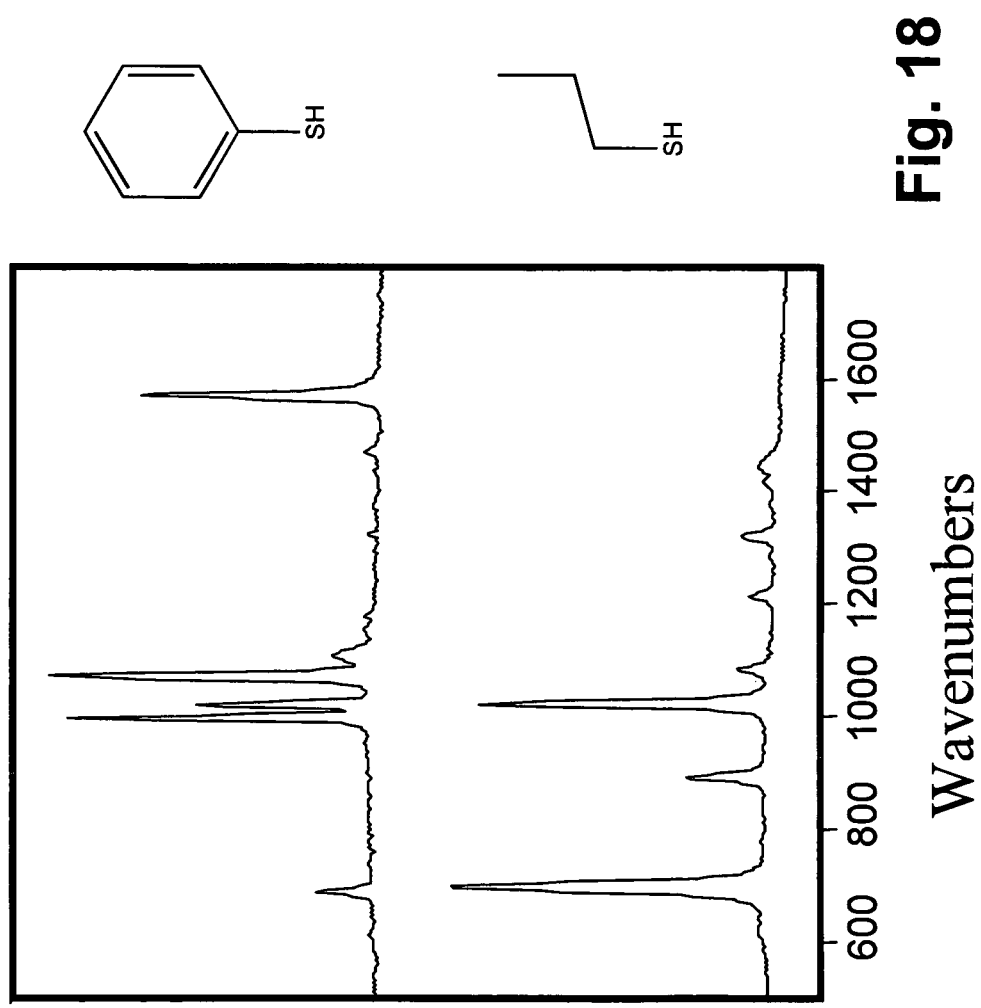
FIG. 18 is a schematic diagram of exemplary Raman spectra for two analytes identified in an assay indicating the uniqueness of the spectra for each particular molecule.
Figure 19:
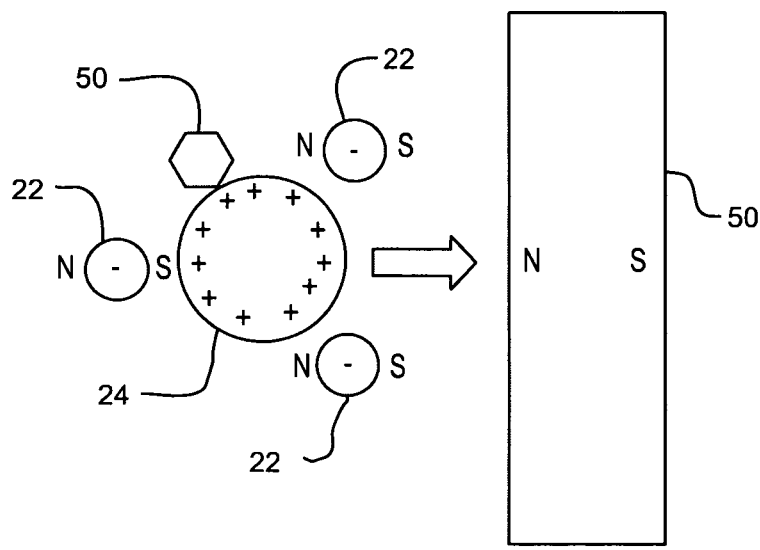
FIG. 19 is a schematic diagram depicting a binding event between spectral enhancement particle and paramagnetic particles for use in a Raman spectroscopy chemical assay according to an alternate embodiment of the invention.

FIG. 18 depicts the Raman spectra of several analytes, particularly thionol and propane thiol. As described above, in the context of the present invention, Raman spectra can be used simply as markers for assays. The position and intensity of the Raman spectrum at a particular wave number can be translated into lines of relative position and thickness. Recognizing that each particular molecule exhibits a unique Raman spectrum, a unique barcode can be correlated to each molecule of interest as an analyte. This concept of barcodes allows for simple storage of analytical identification information for any compound with a unique Raman spectrum and comparison of such stored information with the Raman spectrum of an unknown sample to quickly render an assay.

The tethered paramagnetic particles described above offer an elegant solution to the complex problem of concentrating analytes attached to spectral enhancement particles. However, alternatives to using tether compounds to bind the paramagnetic particles 22 and spectral enhancement particles 24 can be substituted. In one embodiment shown in FIG. 19, a mixture of paramagnetic particles 22 and spectral enhancement particles 24, e.g., silver nanoparticles, may naturally bind together. This results from the hydroxyl surface of paramagnetic particles creating a Zeta potential that is opposite to that of the silver nanoparticles. For example, silver nanoparticles can be coated with citrate anions, while paramagnetic particles are neutralized by cations. The analyte 50 is again bound to the spectral enhancement particle by a chemical tether.

Figure 20:
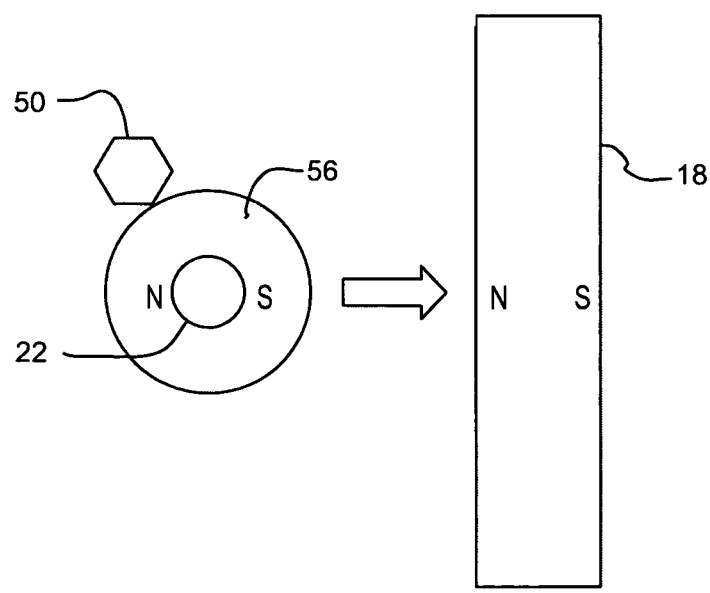
FIG. 20 is a schematic diagram depicting a paramagnetic particle coated with a spectral enhancement metal for use in a Raman spectroscopy chemical assay according to a further embodiment of the invention.
Figure 21:
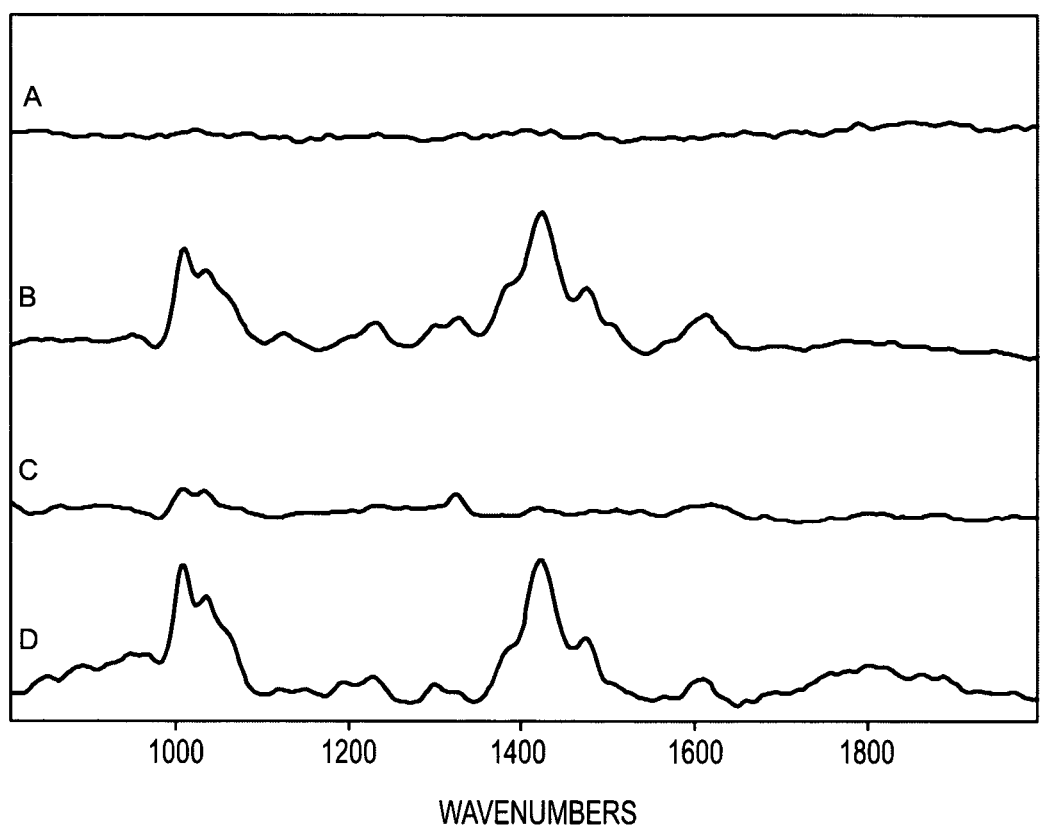
FIG. 21 is a schematic diagram of a set of related Raman spectra for an analyte bound to a paramagnetic particle coated with a spectral enhancement metal.

In another embodiment depicted in FIG. 20, the paramagnetic particle 22 may be covered with a spectral enhancement coating 56. For example, a citrate reduction of $Ag^+$ in the presence of paramagnetic particles creates a silver coated paramagnetic particle. Although this embodiment is possible, it is well known that an absorptive dielectric, such as a paramagnetic particle core, will dampen the SERS effect and thus this form of the invention may not be preferred. Although potentially dampened, FIG. 21 illustrates that a sufficient Raman spectrum assay may still be achieved by this embodiment. FIG. 21 depicts a series of related spectra of 0.05 M of pyridine attached to silver coated paramagnetic particles. Raman spectrum A is of the coated paramagnetic particles only. Spectrum B is of pyridine attached to the coated paramagnetic particles in solution. Spectrum C is of the supernatant after the application of a magnetic field to remove the pyridine-particle adduct. Spectrum D is of a concentrated pellet of the pyridine-particle adduct created by a magnetic field. Thus, by concentrating the analyte adsorbed to silver coated paramagnetic particles, the dampening effect of the paramagnetic particles can be effectively countered.

Figure 22:
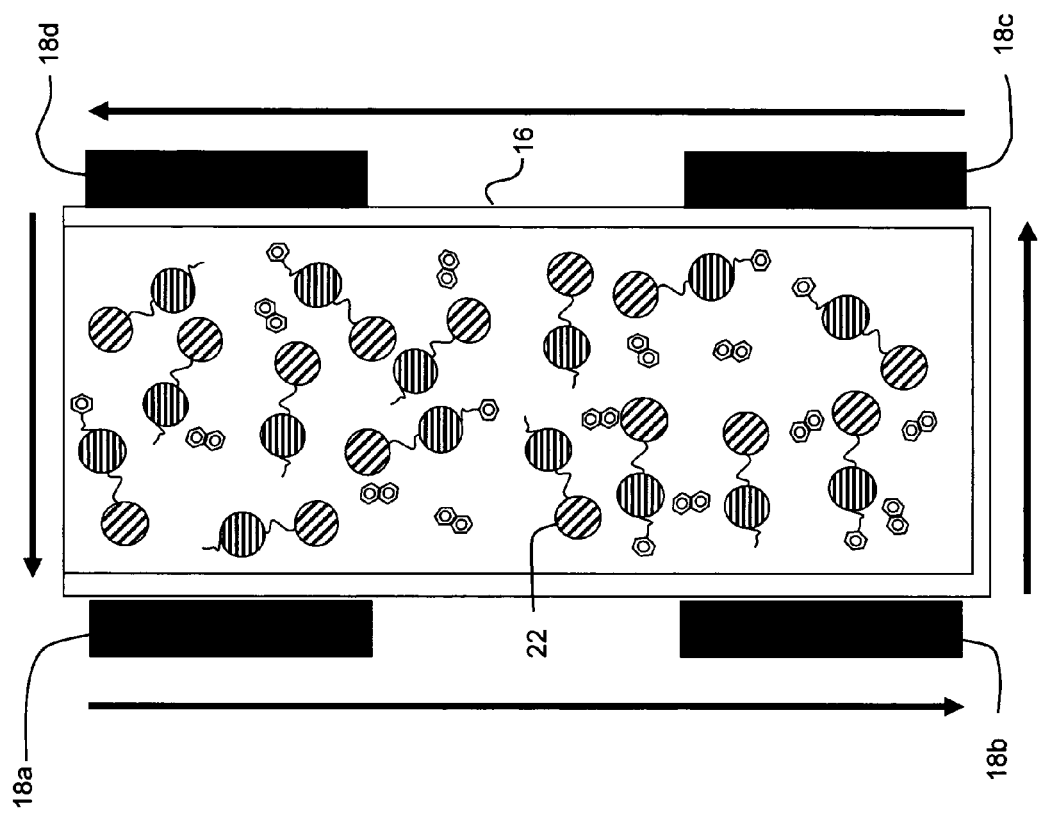
FIG. 22 is a schematic diagram depicting a method for magnetic convention of a sample solution according to another embodiment of the present invention.

FIG. 22 illustrates another novel aspect of the present invention, that of motive convection. Any assay requires mixing to bring the reagents in contact with the analyte. This invention improves on shaking or stirring by using magnetic fields to move the particles around and to create a stirring effect within the sample chamber 16. In this embodiment, a plurality of electromagnets 18*a*, 18*b*, 18*c*, 18*d*, in addition to the assay focusing magnet, are positioned at various locations about the sample chamber 16. By alternately powering the electromagnets 18*a*, 18*b*, 18*c*, 18*d* the paramagnetic particles 22 will be attracted to the magnetic fields created, thus moving the paramagnetic particles 22 throughout the sample chamber 16 to create a stirring effect. For example, electromagnet 18*a* can be first activated, then deactivated in favor of the activation of electromagnet 18*b*. Electromagnet 18*b* is then deactivated in favor of the activation of electromagnet 18*c*. Electromagnet 18*c* is then deactivated in favor of the activation of electromagnet 18*d*. Electromagnet 18*d* is then deactivated in favor of the activation of electromagnet 18*a*, and so on in continuing succession. In this manner, a current or stirring action is induced within the sample chamber 16 in the direction of the arrows in FIG. 22.

Another form of the present invention provides a significant advantage over a lateral flow immunoassay discussed above. Recall that with a lateral flow immunoassay a sample must be placed on a card. Then, after some period of time, user then reads the assay. It is thus a two step process and usually the read step is a visual affirmation. In contrast, the present invention describes a fluidic scheme with spectral enhancement particles and paramagnetic particles in solution. When an analyte (antigen) is present, the two particle types become coupled and the paramagnetic particle provides a potential motive force if a magnetic field is present. The magnetic field immobilizes the particle pairs bound to the analyte such that it can be observed by the Raman device.

Additionally, the magnetic field can be switched on and off with an electrical signal, i.e. it could be an electromagnet. That means that the fluidic system can be a continuous loop flowing past the Raman detection system. Periodically the electromagnet can be switched on to immobilize the paramagnetic particles. If an antigen is not present, no Raman spectrum resulting from the spectral enhancement particle above background or negative control levels will be observed. When the magnetic field is switched off, the particles are free to flow through the system loop seeking an analyte/antigen and couple with a spectral enhancement particle and paramagnetic particle. The result is an effective continuous sampling system. The continuous sampling system could be placed in water systems, public areas to continuously monitor for pathogens (e.g., biological threats), in food preparation areas to monitor food safety, or in medical settings to monitor for spread of disease. An exemplary application for such a continuous sample assay would be monitoring in an HVAC (heating, ventilation, and air conditioning) system in a facility. It could also be portable by using a small syringe to pull the air though the filter.

Figure 23:
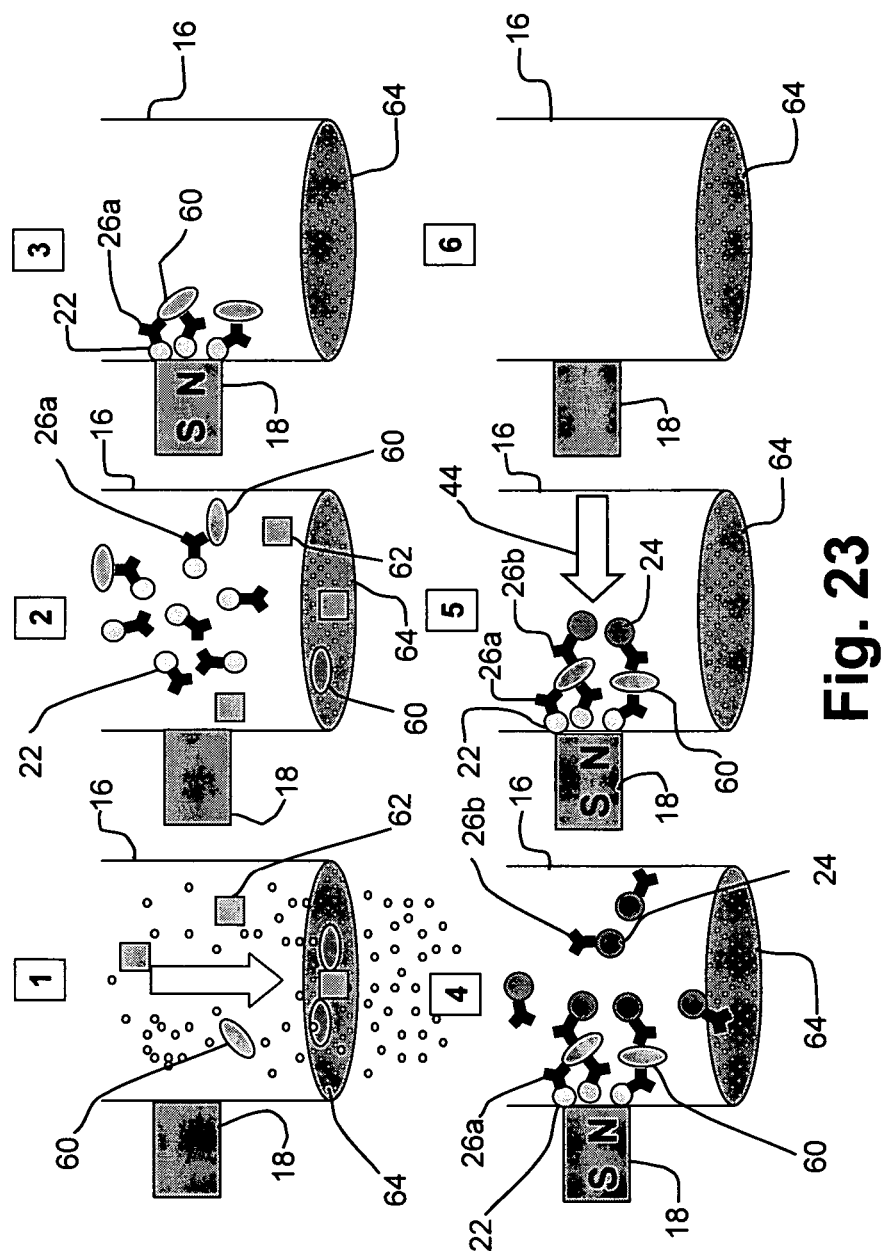
FIG. 23 is a schematic diagram of a process for semi-continuous sampling of fluid for the presence of an antigen according to an additional embodiment of the invention.

FIG. 23 depicts an embodiment of the present invention used in a semi-continuous sampling mode. Scene 1 depicts air being sampled through a water tight air permeable membrane 64. Gore-Tex is a typical material for this type of membrane 64. Microbes and dust collect on the filter. Scene 2 depicts a solution of paramagnetic particles 22 being added to the sample chamber 16. If any microbes 60 with an affinity for the antibodies 26*a* on the paramagnetic particles 22 are present, they will attach to the paramagnetic particles 22. Microbes 62 without an affinity for the antibodies 26*a*, however, will not attach to the paramagnetic particles 22. Scene 3 depicts activation of an electromagnetic and the paramagnetic particles 22 being collected by the magnetic field generated by the electromagnet 18. The remaining solution is removed. Scene 4 depicts a solution of spectral enhancement particles 24 being added. If the antibodies 26*b* on the surface of the spectral enhancement particles 24 have an affinity for the microbes attached to the paramagnetic particles 22, they bind with the paramagnetic particles 22 via the microbes 60 and will become localized by the magnetic field. Scene 5 depicts a laser beam 44 being used to interrogate the particles and microbes 60 localized by the magnetic field. If the spectral enhancement particles 24 are present a Raman spectral signal corresponding to one or more spectral flag compounds associated with the spectral enhancement particles or to the microbes 60 themselves will be generated. Scene 6 depicts the deactivation of the magnetic field to prepare the container for another sample cycle.

It should be noted that continuous and semi-continuous liquid sampling procedures may also be performed according to the steps described above. In this context, the membrane of the sample container would be exchanged for a solution filter system. An exemplary solution filter may be a Nuclepore® filter.

EXAMPLE

Chemical Specific Coating Detection of Neurotransmitters

Neurotransmitters are important to the nervous system of invertebrates and vertebrates. Consequently, measurement of neurotransmitter release and uptake is a central concern in neurochemistry and pharmacology. In-vivo microdialysis has been the most prevalent method for studying neurotransmitter chemistry in the extracellular fluid (ECF) of the brain. This method administers pharmaceuticals through dialysis tubing while simultaneously collecting ECF from a specific area of the brain. Neurotransmitters are usually monitored in this method using High Performance Liquid Chromatography (HPLC) and electrochemical detection. Work has also been done with in-vivo and ex-vivo microdialysis using silver electrodes as SERS substrates, although proteins from the biological matrix can cause interferences.

Studies of the mechanism of psychotropic drugs such as antipsychotic, antidepressant, and anxiolytic drugs provide the greatest amount of information when the study can yield precise characterization of the drug-induced temporal changes of extracellular concentrations of key neurotransmitter s such as dopamine (DA), noradrenalin (NA), serotonin (5-HT), and acetylcholine (ACh), as well as amino acids such as glutamate and gamma-amino-butyric acid (GABA). Changes in extracellular concentrations of these neurotransmitters are believed to reflect changes in neurotransmission mediated by action at specific receptor subtypes, maintaining that the blockade of some receptors by these drugs will determine net transmission. However, in all methods to date, real-time monitoring has been impossible due to the time required for sample collection and chromatographic separation and/or biological interferences.

Intracerebral microdialysis of conscious free-moving animals (and man, during neurosurgery or with permanent shunts in the ventricles) with chemical detection methods that have the requisite sensitivity and reliability is an ideal means to achieve the linkage of release of neurotransmitters, amino acids, and peptides and behavior. For example, using microdialysis, it has been established that atypical antipsychotic drugs such as clozapine, risperidone, olanzapine and ziprasidone, produce a preferential increase in extracellular dopamine concentrations in a rat medial prefrontal cortex compared to the nucleus accumbens and striatum. These findings may provide a strong explanation as to how these drugs are able to improve cognition and negative symptoms in schizophrenia. This approach provides the ability to develop more effective drugs for these symptoms and cognitive disorders in general. Future studies relating these effects on neurotransmission to behaviors such as prepulse inhibition and working memory, social interaction, etc., would be greatly aided by a method to measure the concentrations of these and other neurotransmitters and neuromodulators in real-time.

In microdialysis experiments the dialysate sample volume is determined by perfusion flow rate. The collection interval is adjusted to provide adequate sample volume to be safely within the detection limit. The flow rate of the perfusion medium, an artificial cerebrospinal fluid, usually varies from 0.5 to 2 µl/min. The collection interval may be from 15 to 30 min, which yields 12 to 60 µl per sample. Traditional analysis methods employed HPLC or electrochemical detection for quantification. This is problematic because there are significant time differences, or dissociation, between extracellular concentrations of neurotransmitter s and behavioral changes. In addition, most laboratories have been unable to measure more than one neurotransmitter at a time. Although methods to simultaneously measure multiple neurotransmitter s have been reported, they are technically difficult and require expensive equipment. Because of the limitation of sampling to intervals of 15-30 min. and often longer, only relatively long-lasting effects of drugs and/or behavioral manipulation on extracellular neurotransmitter concentrations can be measured. This has limitations due to the significant time lags or dissociation between extracellular concentrations of neurotransmitter s and behavioral changes. The real-time ex-vivo observation of spatial and temporal changes in neurotransmitter levels as a function of drug therapy or environmental stimuli is vital to understanding basic psychochemical processes.

Figure 24:
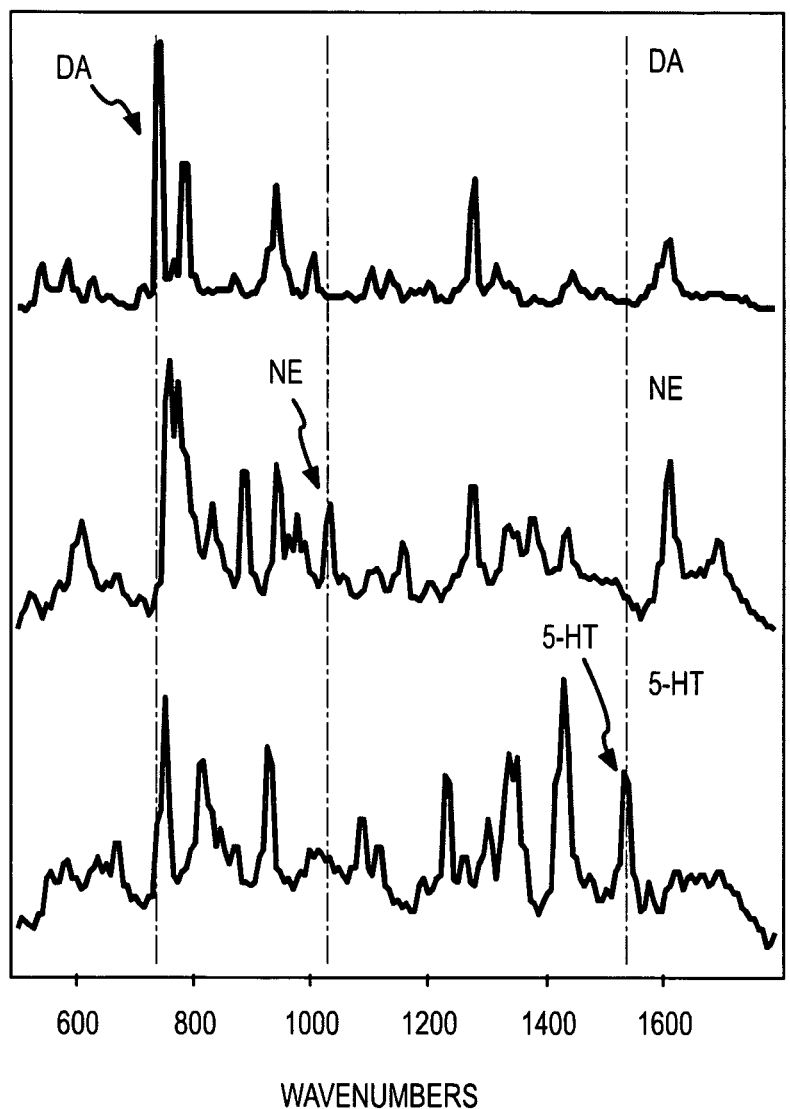
FIG. 24 is a schematic diagram depicting a series of Raman spectra for samples of the neurotransmitters dopamine (DA), norepinephrine (NE), and serotonin (5-HT).

FIG. 24 shows the normal Raman spectra of the some of the primary neurotransmitters, dopamine (DA), serotonin (5-HT), and norepinephrine (NE). Most evident are the distinguishing peaks in each of the compounds. When these same compounds are studied with SERS, a significant increase in sensitivity is observed, but similar distinguishing features are found. The detection of NTs using silver electrodes and gold colloids has been demonstrated. See Morris, M. D.; McGlashen, M. L.; Davis, K. L., Surface-enhanced Raman (SERS) probes of neurotransmitters. *Proceedings of SPIE—The International Societyfor Optical Engineering* 1990, 1201, (Proc. Opt. Fibers Med. 5, 1990), 447-50; Kneipp, K.; Wang, Y.; Dasari, R. R.; Feld, M. S., Near-infrared Surface-Enhanced Raman Scattering (NIR-SERS) of Neurotransmitters in Colloidal Silver Solutions. *Spectrochimica Acta* 1995, 51A, (3), 481-487. However, a problem when using electrode surfaces is that they can foul up easily and provide irreproducible results. Gold colloids constituted an advance toward an effective assay, but detection levels were above metabolic levels in the dialysate from rat brains.

According to one aspect of the present invention, an experimental approach uses designer coatings that have chemical specificity toward neurotransmitters. The coatings are designed with two reactive sites: one for the neurotransmitter and the other specific to a spectral enhancement particle surface. This technique has the advantages of selectivity due to the reactivity of the coating and the structural specificity of Raman spectroscopy; and high sensitivity due to the concentration of neurotransmitters at the spectral enhancement particle surface and the strong amplification of Raman scattering at spectral enhancement particle surfaces arising from the Surface Enhanced Raman Scattering (SERS) effect.

The present invention uses the properties of the paramagnetic particles to separate the desired neurotransmitter adducts on silver spectral enhancement particles from the complex matrices that are dealt with in pharmacological research involving the detection of serotonin during the study of atypical antipsychotic drugs such as clozapine and haloperidol. The chemical structure of dopamine, serotonin, norepinephrine all have a common chemical feature; they all contain electron-rich sites on their aromatic rings. This makes these compounds susceptible to reaction with diazoniums to form azo adducts. Azo compounds make up a large number of popular dyes. The azo bridge contains n-π* electronic transitions that provide moderate resonance Raman scattering. The silver spectral enhancement particle provides an enhancement of approximately a factor of $10^7$. The combination of enhancements produces subnanomolar detection limits. Moreover, this process is extremely rapid (approximately 30 seconds) whereas the standard method of high performance liquid chromatography (HPLC) separation and electrochemical detection takes much longer. The HPLC method alone requires approximately 30 minutes per assay.

The physical properties and synthetic methods for creating nanoscale paramagnetic particles are well established. The small paramagnetic particles have found wide application as separation facilitators in techniques such as immunoassays and a wide variety of biomedical applications. Paramagnetic particles are composed of materials with an unpaired electron. For example, $Fe^{3+}$ ions have 5 unpaired electrons. This has a very strong paramagnetic reaction to a magnetic field. In general, assay material that reacts positively with a magnetic field and has a small susceptibility with a field is termed paramagnetic.

Silver particles can be kept at a very low concentration to keep the surface coverage of tethered serotonin high. The coupling of the silver particles with paramagnetic particles permits a dilute solution of SERS active particles to be concentrated. This makes it possible to detect several orders of magnitude lower concentration of neurotransmitters than with the existing method. It has been shown that with a decrease of coverage there is an increase in the SERS enhancement. In addition, the presence of excess silver nanoparticles that do not have analyte attached to the surface can adsorb and/or scatter the Raman photons. Selectively attaching analytes to the surface of silver nanoparticles allows for a high surface coverage at low analyte concentrations. Finally, the concentration of particles from a dilution solution/matrix will also allow for removing the SERS active portion of the assay from interferences such as ECF proteins. The chemical process of the present invention creates a neurotransmitter adduct that produces an additional resonant Raman enhancement of as much as an additional thousandfold improvement in sensitivity. Brownian motion of the nanoparticles mimics agitation and naturally mixes the reagents throughout the sample. This combination of enhancements and comprehensive sample measurement has led to subnanomolar detection limits.

In this experiment, a diazonium is reacted with one of these neurotransmitters and is adapted to be bifunctional with a group that can also attach to spectral enhancement particles, in this case silver nanoparticles, for SERS analysis. A number of diazoniums have been examined. To date, the best results have come with the 0507 tether (Corcoran Research Group, University of Wyoming). The number refers to the date at which the tether synthesis was finished. The structure of the 0507 tether is shown in FIG. 25. Note, the 0507 tether contains the appropriate diazonium group for reaction with the neurotransmitter and a benzyl sulfide to attach to the silver colloid. Benzyl sulfides tend to cleave to leave a benzyl radical and thiolate attached to the silver surface.

An exemplary assay for serotonin according to the present invention is now described. Nanoscale paramagnetic particles may be produced using an accepted method of coprecipitation of $Fe^{3+}$ and $Fe^{2+}$ in 6N NaOH at 85° C. Equal molar equivalents of ferrous ammonium sulfate and ferric ammonium sulfate are added to 400 ml of deionized $H_2O$. The solution is then brought to between 85-90° C. and 850 ml of 6N NaOH is added over 90 minutes. The resulting precipitated particles are separated and washed using a centrifuge. Each aliquot of the particle solution is centrifuged at approximately 250 G for ten minutes. The resulting supernatant is removed and the pellet is resuspended in Millipore water. This procedure is repeated until the resulting solution is approximately pH 7.

The neutral paramagnetic particles are then coated by a reduction of silver nitrate on to the paramagnetic surface using a citrate reduction analogous to a Lee and Meisel procedure. (Lee, P. C.; Meisel, D., Adsorption and surface-enhanced Raman of dyes on silver and gold sols. *Journal of Physcial Chemistry* 1982, 86, (17), 3391-5.) Ninety (90) mg of silver nitrate is added to 500 mL of the neutral paramagnetic particle solution in a 1000 mL Erlenmeyer flask equipped with a large stir bar. The solution is brought to a boil and 10 mL of 1% sodium citrate is added. The solution is allowed to boil for 1 hr. The paramagnetic particles act as aggregation sites for the reduction of the silver nitrate. After 1 hr of boiling the black solution of PP becomes reddish-brown indicating a change in the optical properties of the solution. Once cool, the volume is brought back to 500 ml.

The neurotransmitter specific coating is prepared by diazotizing 1.5 mg of a stock $5.0 \times 10^{-3}$ M solution of the 0507 tether (Corcoran Research Group, University of Wyoming) (as the stable amine) in a 1-dram screw top vial. Nine hundred (900) µL of absolute ethanol purchased from Aldrich and 100 µL of p-toluene sulfonic acid solution (PTSA, 100 mg/mL in absolute ethanol) is added to the 1.5 mg of the 0507 tether. This solution is stirred with a micro-stir bar in an ice bath in a refrigerator at 0° C. for 30 minutes. To form a diazonium, 2 µL of butyl nitrite is added to the reaction mixture and stirred for an additional 30 minutes. If stored below 0° C., this stock solution of diazotized tether can last for 2-3 days. A yellow or rose color indicates the solution is no longer active. The 0507 tether solution is further diluted to $1.0 \times 10^{-4}$ M with Millipore water for use in experiments. The addition of water also reduces the appearance of ethanol peaks in the Raman spectra. The characteristic peaks of the 0507 tether are identified in the Raman spectrum from a blank consisting of 100 µL of the 0507 tether and 900 µL of silver-coated, paramagnetic nanoparticle colloid.

The next step is to determine the reactivity of serotonin with the 0507 tether and determine a detection limit. A $1.0 \times 10^{-3}$ M stock solution of serotonin is prepared with 2.1 mg of serotonin (Aldrich) diluted with 10 mL of 1.0 M Dulbecco's phosphate buffer (Aldrich). Subsequent dilutions ranging in concentration from $1.0 \times 10^{-4}$ M to $1.0 \times 10^{-10}$ M are made in 1-dram vials and diluted with the Dulbecco's buffer. A 0.1 M solution of sodium borohydride is used to reduce the excess diazonium back to the amine. This form cannot react with itself to form an interfering dye. The solution of sodium borohydride is made by dissolving 3.7 mg of sodium borohydride in 1 mL of 0.5 M sodium hydroxide solution. The borohydride is important as the unreacted 0507 tether can constitute an interference in the assays. By allowing the 0507 tether to react with the serotonin and subsequently adding the borohydride, the excess diazonium is reduced back to the unreactive amine form.

Five hundred (500) µL of each of the $1.0 \times 10^{-4}$ M 0507 tether solution and the serotonin solution, of the different concentrations, are added together in 1-dram vial. An amount of sodium borohydride equal to 1% of the total volume of the solution is then added (10 µL). This is the reaction mixture. In this solution, a reaction between the 0507 tether and analyte occurs and the excess diazonium is converted back to the unreactive amine form. Ten 100 μL samples are created by a serial dilution of this solution in order to provide a concentration range one order of magnitude lower than the original concentration of reaction mixture. To each 100 μL sample, 300 μL of the colloid is added and placed on a vortex for three seconds. This vial is placed into a Raman spectrometer (e.g., a Delta Nu Advantage 200A Raman instrument). A Raman spectrum indicative of the seratonin is acquired within an average of 5-1 second acquisitions.

ECF cerebral samples are collected from living rats by inserting microdialysis probes into the rats' brains. Probe positions on the rats' heads corresponding to the desired region of the brain are located and small holes are drilled into their skulls. Perfusion cannulae are inserted into these holes and dialysate is pushed through the cannulae for four days to remove blood due to the surgery. These samples are analyzed in the same prepared manner as the standards, however, in smaller volumes due to the low volume produced in experiments. The lower volumes may require a scaling down of the volumes used in the standard procedure. Five (5) μL of the dialysate is added to 5 μL of the $1.0 \times 10^{-4}$ M 0507 tether in a microtiter plate well. Sixty (60) μL of colloid is added to the reaction mixture. The sample is placed into a capillary tube in order to accommodate the small sample volume. The capillary sample is placed into the capillary tube adapter for the Raman spectroscopy instrument.

Figure 26:
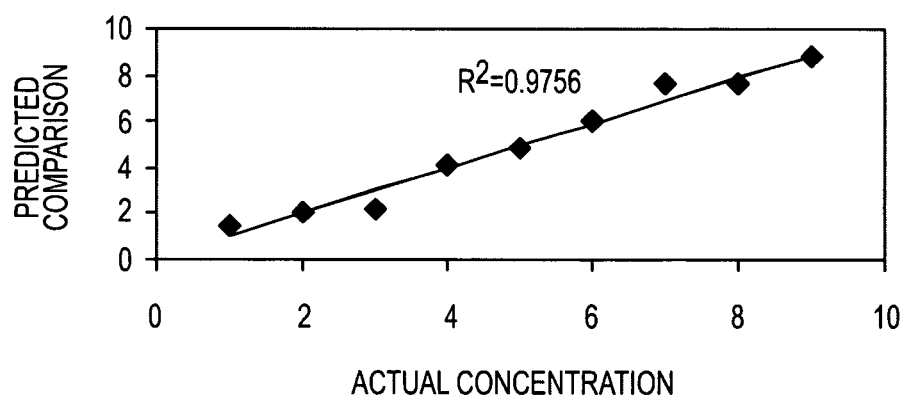
FIG. 26 is a graph plotting actual concentration of serotonin measured by Raman spectroscopy against predicted concentrations.
Figure 27:
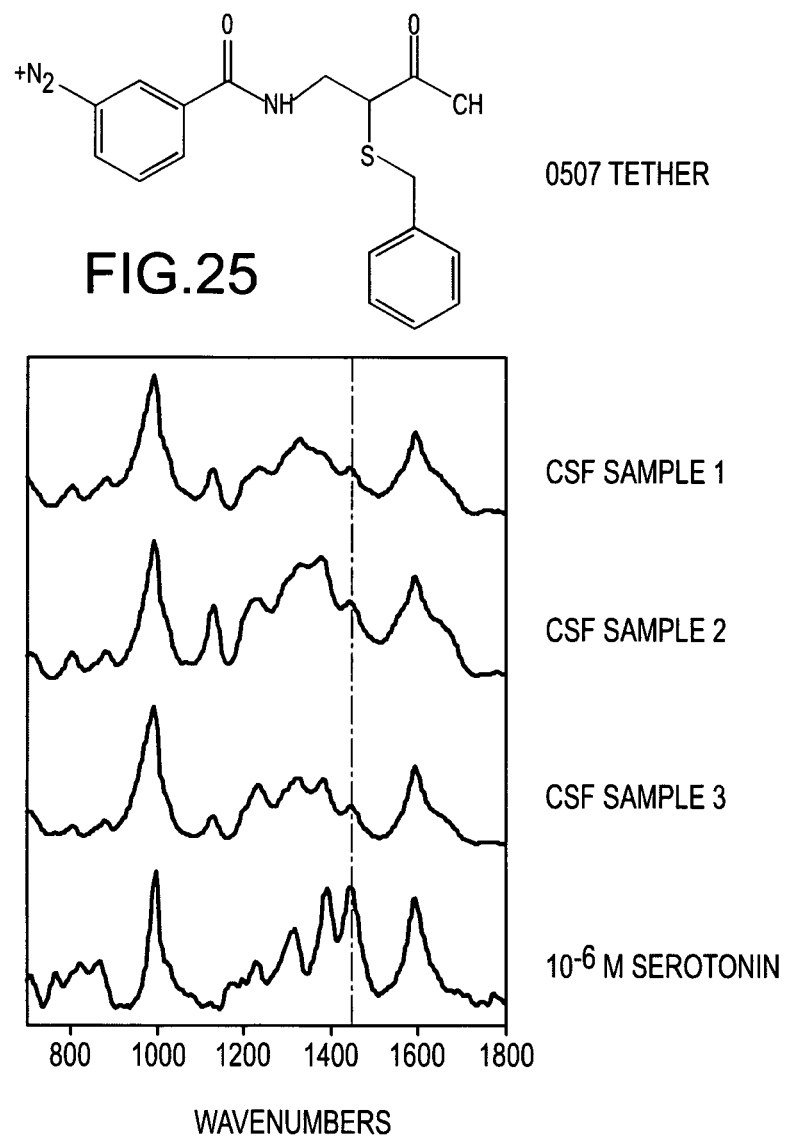
FIG. 27 is a schematic diagram depicting a series of Raman spectra for samples of serotonin joined by a chemical tether to a spectral enhancement particle as compared to the Raman spectrum of isolated serotonin.

Grams 32 and PLSIQ algorithms (Thermo-Galactic) are used to determine the correlation between the spectral features and the concentration of serotonin in ECF samples. The wavelength range best suited for serotonin between 1390 to 1450 $cm^{-1}$. FIG. 26 shows the correlation between actual serotonin concentrations and predicted concentrations. At a concentration of $1.0 \times 10^{-9}$ M serotonin, the $R^2$, or determination value, in the model was 0.9756 and the detection limit was $1.00 \times 10^{-10}$ M (3× signal to noise). FIG. 27 depicts several spectra of the 0507 tether reacted with serotonin in the ECF (notated as CSF Samples 1-3) along with a $1 \times 10^{-6}$ M serotonin/tether spectrum in a buffered solution to show the correlation between ECF samples and a control. The peaks of interest can still be seen in the ECF samples and thus the concentration of serotonin level can be determined by the PLS algorithm.

In an alternative methodology, the paramagnetic particles can be chemically tethered to spectral enhancement particles. Nanoscale spinel iron oxide paramagnetic particles are again prepared as described above. However, instead of coating the paramagnetic particles with a SERS reactive metal, the paramagnetic particles are chemically tethered to a SERS reactive nanoparticle. SERS reactive silver nanoparticles are prepared using by a modified Lee and Meisel procedure. (Lee, P. C.; Meisel, D., Adsorption and surface-enhanced Raman of dyes on silver and gold sols. *Journal of Physcial Chemistry* 1982, 86, (17), 3391-5.) Ninety (90) mg of silver nitrate is dissolved in 500 mL of water in a 1000 mL Erlenmeyer flask equipped with a large stir bar. The solution is brought to a boil and 10 mL of 1% sodium citrate is added. The solution is boiled for an additional 30 minutes. The solution is then removed from the heat and allowed to cool to room temperature while continuing to stir. Once cool, the solution is rediluted to 500 ml.

The neurotransmitter specific coating for the silver nanoparticles is prepared by diazotizing 1.5 mg of a 0507 amine precursor (Corcoran Research Group, University of Wyoming) (as the stable amine) in a 1-dram screw top vial to create a $5 \times 10^{-3}$ M solution of the activated 0507 tether. Nine hundred (900) μL of absolute ethanol purchased from Aldrich and 100 μL of p-toluene sulfonic acid solution (PTSA, 100 mg/mL in absolute ethanol) is added to 1.5 mg of the 0507 amine precursor. This solution is stirred with a micro-stir bar in an ice bath in a refrigerator at 0° C. for 30 minutes. To form a diazonium, 2 μL of butyl nitrite is added to the reaction mixture and stirred for an additional 30 minutes.

Figure 28:
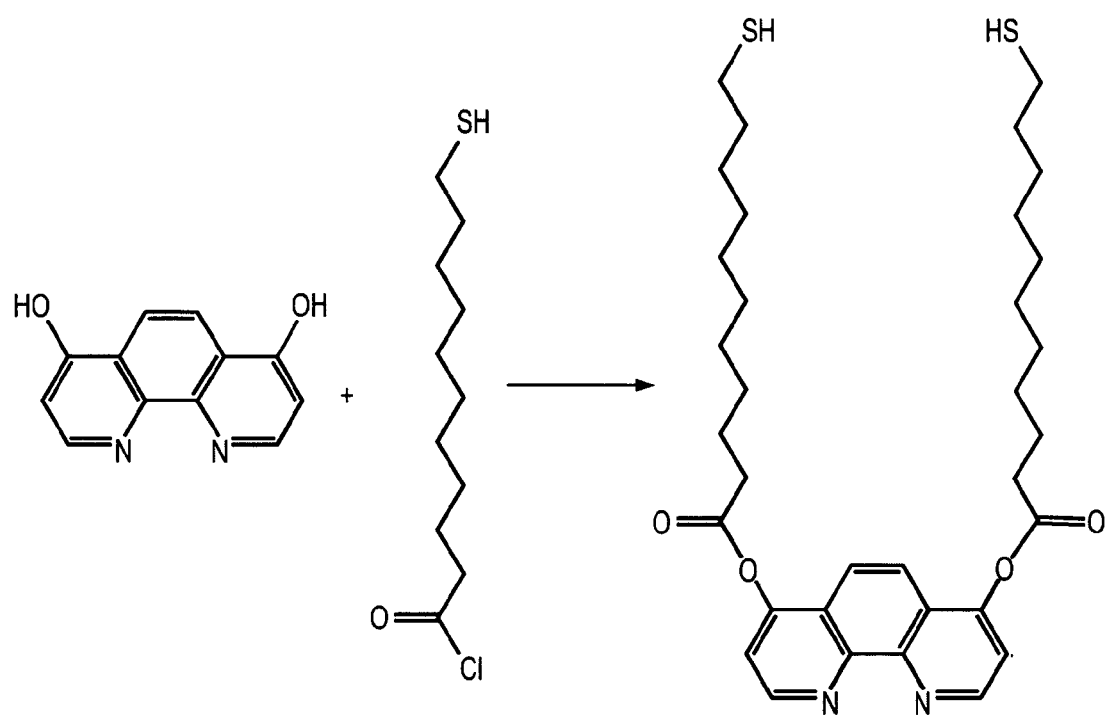
FIG. 28 is a schematic diagram depicting an exemplary chemical tether for joining a paramagnetic particle to a spectral enhancement particle.

An equimolar amount of paramagnetic particles is then added to the tether solution with the SERS reactive silver particles. A chemical tether designed to join the paramagnetic particles to the silver particles is also added to the solution. An exemplary tether is a 1,10-phenanthroline-4,7-diol (Aldrich) coupled by mercaptoundecanoic acid chloride synthesized from mercaptoundecanoic acid (Aldrich) as shown in FIG. 28. This phenanthroline compound will bind strongly to the paramagnetic particles through the 1,10-phenanthroline and to the silver nanoparticles through the thiols. A fifty (50)-fold excess of the phenanthroline compound is added to the particle solution. The tethered particle solution is further diluted to $1.0 \times 10^{-4}$ M with Millipore water for use in experiments to detect serotonin levels in samples as described above.

Conceptually, one can see how the ultimate limit of detection occurs with free floating silver colloidal particles. As the amount of serotonin decreases the coverage of serotonin tethered to the surface of a spectral enhancement particle decreases to the point of one or less per particle. One could decrease the number of silver particles to decrease the active SERS surface area. This would make the number of analytes tethered per spectral enhancement particle higher. But again a limit is rapidly reached where there are insufficient particles in the laser beam to produce a good signal.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attach, couple, connect, bind, and join) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A method for performing an assay to determine the presence of at least one analyte, comprising:
   binding in solution within a sample chamber at least one of a plurality of spectral enhancement particles, at least one of a plurality of paramagnetic particles including a coating, and at least one analyte to form a combination product, wherein the spectral enhancement particles bind with the at least one analyte or the paramagnetic particles and the paramagnetic particles bind with the at least one analyte or the spectral enhancement particles, should the at least one analyte be present in the solution;

applying a magnetic field to the solution from a magnet positioned adjacent the sample chamber;

concentrating at least a portion of any combination product and at least a portion of the plurality of paramagnetic particles not part of the combination product in the solution into a condensation at a discrete location within the sample chamber using the influence of the magnetic field;

interrogating the discrete location within the sample chamber with a laser beam to obtain spectral information, wherein the interrogation laser beam is passed through the sample chamber to the discrete location within the sample chamber and a Raman scattered light signal including the spectral information is passed back through the sample chamber;

receiving the Raman scattered light signal including the spectral information from the sample chamber; and using the spectral information to detect the presence of, quantify the amount of, or both detect the presence of and quantify the amount of, said at least one analyte in the solution, wherein the spectral information comprises spectral information derived from the coatings of the plurality of concentrated paramagnetic particles and the spectral information derived from the coatings of the paramagnetic particles is used as an internal standard in the detection operation.

2. The method of claim 1 wherein
the spectral information is a Raman spectrum from Raman scattered light from the discrete location.

3. The method of claim 2, wherein
the assay is an immunoassay;
the at least one analyte is at least one antigen;
at least a first portion of the spectral enhancement particles are connected with a first antibody specific to the at least one antigen and a spectral flag compound; and
at least a first portion of the paramagnetic particles are connected with a second antibody specific to the at least one antigen; and wherein the step of binding further comprises
binding the first portion of the paramagnetic particles to the first portion of the spectral enhancement particles via the at least one antigen when the spectral enhancement particles with the first antibody and the paramagnetic particles with the second antibody are in the presence of the at least one antigen.

4. The method of claim 3 further comprising determining whether the spectral flag compound is present in the discrete location as a result of the binding of the first portion of the paramagnetic particles to the first portion of the spectral enhancement particles via the at least one antigen by analyzing the Raman spectrum for a signature spectrum of the spectral flag compound.

5. The method of claim 4 further comprising indicating the presence or absence of the antigen in the solution based upon the presence or absence, respectively, of the signature spectrum of the spectral flag compound.

6. The method of claim 4, wherein
the at least one antigen comprises a plurality of antigens;
the plurality of spectral enhancement particles includes a plurality of subsets of the spectral enhancement particles, wherein each of the subsets is connected with a respective antibody specific to a respective one of the plurality of antigens and a respective spectral flag compound unique to the respective subset; and
the plurality of paramagnetic particles includes a plurality of subsets of the paramagnetic particles, wherein each of the subsets is connected with a respective antibody specific to a respective one of the plurality of antigens; and wherein
the step of binding further comprises binding respective subsets of the paramagnetic particles to respective subsets of the spectral enhancement particles via respective ones of the
plurality of antigens; and
the step of determining further comprises detecting the presence of, quantifying the amount of, or both detecting the presence of and quantifying the amount of the one or more spectral flag compounds in the solution.

7. The method of claim 3, wherein the first antibody is the same as the second antibody.

8. The method of claim 2 further comprising magnifying the amplitude of the Raman scattered light through the presence and influence of the spectral enhancement particles.

9. The method of claim 2 further comprising translating the Raman spectrum into a barcode.

10. The method of claim 2 further comprising semi-continuously or continuously introducing the solution into a sampling chamber.

11. The method of claim 2, wherein
the assay is a chemical assay;
the solution comprises a plurality of first tethers, each of the first tethers having a first binding end with an affinity for the spectral enhancement particles and a second binding end with an affinity for the paramagnetic particles;
the solution further comprises a plurality of second tethers, each of the second tethers having a first binding end with an affinity for the spectral enhancement particles and a second binding end with an affinity for the analyte; and wherein the step of binding further comprises
binding the paramagnetic particles to the spectral enhancement particles via the first tethers; and
binding the spectral enhancement particles to the analyte via the second tethers in the circumstance the analyte is in the solution.

12. The method of claim 11 further comprising analyzing the Raman spectrum for a signature spectrum of the analyte.

13. The method of claim 12, wherein
the at least one analyte comprises a plurality of analytes; and
the plurality of second tethers comprises a plurality of subsets of the second tethers, wherein each the of the subsets has a unique second binding end that is specific to a respective one of the plurality of analytes.

14. The method of claim 11 further comprising indicating the presence or absence of the analyte in the solution based upon the presence or absence, respectively, of a signature spectrum of the analyte.

15. The method of claim 1 further comprising varying the magnetic field to pull the combination product and the plurality of paramagnetic particles not part of the combination product in multiple directions within the solution, wherein the varied magnetic field creates a mechanical convection within the solution.

16. The method of claim 1, wherein the solution is chosen from liquid and air.

17. The method of claim 1, wherein the condensation comprises a concentrated ball of particles.

18. The method of claim 1 wherein the operation of interrogating the discrete location within the sample chamber comprises (i) generating a laser beam, (ii) focusing a first portion of the laser beam through a focusing lens to direct the first portion of the laser beam through the sample chamber to the discrete location within the sample chamber, (iii) redirecting a second portion of the laser beam to a Raman analyzer, (iv) receiving the Raman scattered light signal at the Raman analyzer, and (v) comparing the redirected second portion of the laser beam and the Raman scattered light signal to determine the spectral information.

* * * * *